US009827301B2

(12) United States Patent
Costantino et al.

(10) Patent No.: US 9,827,301 B2
(45) Date of Patent: Nov. 28, 2017

(54) HYPO- AND HYPER-ACETYLATED MENINGOCOCCAL CAPSULAR SACCHARIDES

(71) Applicant: NOVARTIS AG, Basel (CH)

(72) Inventors: Paolo Costantino, Siena (IT); Francesco Berti, Siena (IT)

(73) Assignee: GLAXOSMITHKLINE BIOLOGICALS S.A., Rixensart (BE)

(*) Notice: Subject to any disclaimer, the term of this patent is extended or adjusted under 35 U.S.C. 154(b) by 205 days.

(21) Appl. No.: 14/267,248

(22) Filed: May 1, 2014

(65) Prior Publication Data

US 2014/0234368 A1 Aug. 21, 2014

Related U.S. Application Data

(62) Division of application No. 10/574,437, filed as application No. PCT/IB2004/003366 on Oct. 4, 2004, now abandoned.

(30) Foreign Application Priority Data

Oct. 2, 2003 (GB) .................................. 0323103.2

(51) Int. Cl.
| | | |
|---|---|---|
| A61K 39/00 | (2006.01) | |
| A61K 39/095 | (2006.01) | |
| A61K 31/715 | (2006.01) | |
| C08B 37/00 | (2006.01) | |
| A61K 39/05 | (2006.01) | |
| A61K 39/08 | (2006.01) | |
| A61K 39/09 | (2006.01) | |
| A61K 39/02 | (2006.01) | |
| A61K 39/102 | (2006.01) | |
| A61K 39/13 | (2006.01) | |
| A61K 39/29 | (2006.01) | |
| A61K 39/295 | (2006.01) | |

(52) U.S. Cl.
CPC .......... *A61K 39/095* (2013.01); *A61K 31/715* (2013.01); *A61K 39/05* (2013.01); *A61K 39/08* (2013.01); *A61K 39/092* (2013.01); *A61K 39/099* (2013.01); *A61K 39/102* (2013.01); *A61K 39/13* (2013.01); *A61K 39/29* (2013.01); *A61K 39/292* (2013.01); *A61K 39/295* (2013.01); *C08B 37/006* (2013.01); *A61K 2039/6037* (2013.01); *A61K 2039/64* (2013.01); *A61K 2039/70* (2013.01)

(58) Field of Classification Search
None
See application file for complete search history.

(56) References Cited

U.S. PATENT DOCUMENTS

| 2005/0106181 A1 | 5/2005 | Constantino | ............... 424/238.1 |
| 2007/0020293 A1 | 1/2007 | Michon et al. | |
| 2009/0117148 A1 | 5/2009 | Costantino | ............... 424/197.11 |
| 2009/0130147 A1 | 5/2009 | Constantino | ............... 424/236.1 |
| 2009/0182129 A1 | 7/2009 | Costantino | ................... 530/411 |

FOREIGN PATENT DOCUMENTS

| WO | WO-02/058737 A2 | 8/2002 |
| WO | 03/080678 | 10/2002 |
| WO | WO-02/091998 A2 | 11/2002 |
| WO | 03/007985 | 1/2003 |
| WO | WO-03/009869 A1 | 2/2003 |
| WO | WO-03/094834 A2 | 11/2003 |
| WO | WO-2004/067030 A2 | 8/2004 |
| WO | WO-2005/000347 | 1/2005 |
| WO | WO-2005/000347 A1 | 1/2005 |

OTHER PUBLICATIONS

Jones et al. (Nov. 7, 2002). "Use and validation of NMR assays for the identity and O-acetyl content of capsular polysaccharides from Neisseria meningitidis used in vaccine manufacture," *J. Pharmaceutical and Biomedical Analysis* 30(4):1233-1247.
Third Party Observations mailed Jan. 18, 2008, for EP App. No. 04791697.8, 2 pages.
Longworth et al. (2002). "O-Acetylation status of the capsular polysaccharides of serogroup Y and W135 meningococci isolated in the UK." *FEMS Immunol Med Micro*, 32:119-123.
Ada et al., (2003). "Carbohydrate-protein conjugate vaccines" Clinical Microbiology and Infection. 9(2):79-85.
Campbell, James D. et al., (2002) "Safety, reactogenicity, and immunogenicity of a tetravalent meningococcal polysaccharide-diphtheria toxoid conjugate given to healthy adults" The Journal of Inf. Diseases, 186:1848-1851.
Claus et al. (2004) "Genetics of capsule O-acetylation in serogroup C, W-135 and Y meningococci." Molecular Microbiology 51 :227-39.
Database record for assignment of US20070020293, recorded Jun. 6, 2006. 1 page.
Decision on Opposition dated May 26, 2015 for EP1678212. 26 pages.
European Pharmacopoeia (1996) "Meningococcal Polysaccharide Vaccine," Third Edition, pp. 1155-157.
Grabenstein et al. (2002) "Immunofacts; Vaccines and immunologies," Facts and Comparisons, pp. 110-114.
Great Britain patent application No. 0323103.2, filed Oct. 2, 2003 by Chiron SRL. 46 pages.
Lemercinier and Jones. (1996). "Full 1 H NMR assignment and detailed 0-acetylation patterns of capsular polysaccharides from Neisseria meningitidis used in vaccine production" Carbohydrate Research, 296:83-96.
Michon et al. (2000) "Structure activity studies on group C meningococcal polysaccharide-protein conjugate vaccines: effect of O-acetylation on the nature of the protective epitope." Dev Biol (Basel). 103:151-60.

(Continued)

*Primary Examiner* — Patricia A Duffy
(74) *Attorney, Agent, or Firm* — Virginia G. Campen

(57) ABSTRACT

Capsular saccharides derived from serogroups W135 and Y of *Neisseria meningitidis* have altered levels of O-acetylation at the 7 and 9 positions of their sialic acid residues, and can be used to make immunogenic compositions. Relative to unmodified native saccharides, derivatives of the invention are preferentially selected during conjugation to carrier proteins, and conjugates of the derivatives show improved immunogenicity compared to native polysaccharides.

22 Claims, 3 Drawing Sheets

(56) References Cited

OTHER PUBLICATIONS

Notice of Opposition filed by Glaxosmithkline Biologicals SA dated Nov. 14, 2012 for EP1678212. 31 pages.
Notice of Opposition filed by Pfizer Inc. dated Nov. 14, 2012 for EP1678212. 27 pages.
Patentee's Response to Oppositions filed by Novartis AG dated Jul. 15, 2013 for EP1678212. 18 pages.
Patentee's Statement of Grounds of Appeal for EP1678212 on behalf of Novartis AG, dated Oct. 1, 2015. 15 pages.
Pollard et al. (2003) "Conference Summary: W135 Meningococcal Disease in Africa," Emerging Infectious Diseases 9:1503-4.
Power of Attorney filed Jul. 6, 2006 for US20070020293. 2 pages.
Rennels, Margaret et al., Oct. 2002 "Dose escalation, safety and immunogenicity study of a tetravalent meningococcal polysaccharide diphtheria conjugate vaccine in toddlers" The Pediatric Infectious Disease Journal, 21(10):978-979.
U.S. Appl. No. 60/480,405 filed Jun. 23, 2003 by Baxter International Inc. 45 pages.
Who (1980) "Requirements of meningococcal polysaccharides," Annex 6, World Health Organization Technical Report Series, pp. 174-184.
Written Submission on behalf of Novartis AG dated Feb. 13, 2015 in EP1678212. 2 pages.
Written Submission on behalf of Pfizer Inc. dated Feb. 13, 2015 in EP1678212. 12 pages.

HYPO- AND HYPER-ACETYLATED MENINGOCOCCAL CAPSULAR SACCHARIDES

RELATED APPLICATIONS

This application is a Divisional application of U.S. application Ser. No. 10/574,437, which is the U.S. National Phase of International Application No. PCT/IB2004/003366, filed Oct. 4, 2004 and published in English, which claims the benefit of United Kingdom Patent Application No. 0323103.2, filed Oct. 2, 2003. The entire teachings of each of the foregoing patent applications are incorporated herein by reference.

All documents cited herein are incorporated by reference in their entirety.

TECHNICAL FIELD

This invention is in the field of meningococcal capsular saccharides and their conjugated derivatives.

SEQUENCE LISTING

This application contains a Sequence Listing which has been submitted via EFS-Web and is hereby incorporated by reference in its entirety. The ASCII copy, created on Apr. 30, 2014, is named 51825USPCTDSEQ.txt, and is 12,753 bytes in size.

BACKGROUND ART

Polysaccharides are important biological molecules and they have been widely used in the pharmaceutical industry for the prevention and treatment of diseases. For example, capsular polysaccharides have been used for many years in vaccines against capsulated bacteria, such as meningococcus (*Neisseria meningitidis*), pneumococcus (*Streptococcus pneumoniae*) and Hib (*Haemophilus influenzae* type B).

To enhance immunogenicity of capsular polysaccharides, particularly in children, conjugate vaccines were developed. These comprise a capsular saccharide conjugated to a carrier protein [e.g. refs. 1-3]. Conjugation converts T-independent antigens into T-dependent antigens.

The capsular saccharide of *Neisseria meningitidis* serogroup W135 ("MenW135") comprises a polymer of sialic acid-galactose disaccharide units:

→4)-D-Neup5Ac(7/9OAc)-α-(2→6)-D-Gal-α-(1→ where "Neu" refers to neuraminic acid, commonly known as sialic acid.

Similarly, the capsular saccharide of *Neisseria meningitidis* serogroup Y (MenY) comprises a polymer of sialic acid-glucose disaccharide units:

→4)-D-Neup5Ac(7/9OAc)-α-(2→6)-D-Glc-α-(1→

In nature, these capsular saccharides have been found to be O-acetylated at some of the 7 and 9 positions of some of the sialic acid residues. O-acetylation of the W135 saccharide was "reported for the first time" in reference 4, with O-acetylation at the O-7 and O-9 positions being reported. Acetylation at the O-7 and O-9 positions was also seen for the serogroup Y saccharide, although the authors noted that previous work had indicated O-acetylation at O-7, O'-3 or O'-4 positions. Further studies on the O-acetyl content of the saccharides was reported in reference 5.

Reference 5 reports that "there is growing body of evidence that O-acetylation is not important to elicit a protective antibody response" for serogroup W135. In contrast, reference 6 reports that there "is evidence that O-acetylation affects the immunogenicity of polysaccharide vaccines". On the premise that "O-acetylation of the CPS [capsular polysaccharide] may not be important in eliciting protective immunity", however, the authors of reference 5 investigated acetylation in serogroups W135 and Y. Among their results, no change in O-acetylation was seen for these two serogroups after storage in basic conditions for 9 days at room temperature.

Reference 7 reported that "the O-acetylation status of the W135 and Y strains" used in tetravalent polysaccharide vaccines "was not reported" previously. The authors went on in reference 8 to report that "little is known about the O-acetylation status of serogroups W135 and Y", and they stated that further work "may provide useful insights into the optimal vaccine formulation", although the nature of such further work and the possible insights were not elaborated. Reference 9 reports that the "relevance of O-acetylation to vaccine development remains uncertain" for serogroup W135. Reference 6 agrees that data "on the impact of O-acetylation on immunogenicity of serogroup W-135 or Y polysaccharides are not available yet" (January 2004).

This confusion and lack of information for serogroups W135 and Y contrasts with the two other serogroups for which saccharide vaccines are currently in use. Variation in the O-acetylation of the *Neisseria meningitidis* serogroup C capsular polysaccharide has been widely reported [10,11], but it does not seem to have any negative impact on immunogenicity, as the Menjugate™ and NeisVac-C™ products are both effective. In contrast, de-O-acetylation of the serogroup A polysaccharide has been associated with a "dramatic reduction in immunogenicity" [12].

It is an object of the invention to provide capsular saccharide derivatives that can be used to make immunogenic compositions, particularly when conjugated to carrier proteins, and particularly for meningococcal serogroups W135 and Y.

DISCLOSURE OF THE INVENTION

Despite the uncertainty concerning the role of O-acetylation in vaccines for meningococcal serogroups W135 and Y, the inventors have found that O-acetylation can indeed be relevant, particularly during preparation of conjugate vaccines. The invention is based on the discovery that modified capsular saccharides derived from MenW135 and MenY having altered levels of O-acetylation at the 7 and 9 positions of the sialic acid residues can be used to make immunogenic compositions. Relative to unmodified native saccharides, derivatives of the invention are preferentially selected during conjugation to carrier proteins. Moreover, conjugates of these derivatives show improved immunogenicity compared to native polysaccharides.

Modified Saccharides

Thus the invention provides a modified serogroup W135 meningococcal capsular saccharide, wherein: (a) ≤x % of the sialic acid residues in the saccharide are O-acetylated at the 7 position; and/or (b) ≥y % of the sialic acid residues in the saccharide are O-acetylated at the 9 position.

Similarly, the invention provides a modified serogroup Y meningococcal capsular saccharide, wherein (a) ≤x % of the sialic acid residues in the saccharide are O-acetylated at the 7 position; and/or (b) ≥y % or ≤z % of the sialic acid residues in the saccharide are O-acetylated at the 9 position.

The value of x depends on the serogroup: for serogroup W135, x is 29 or less (e.g. 28, 27, 26, 25, 24, 23, 22, 21, 20, 19, 18, 17, 16, 15, 14, 13, 12, 11, 10, 9, 8, 7, 6, 5, 4, 3, 2, 1, 0.5 or 0); for serogroup Y, x is 9 or less (e.g. 8, 7, 6, 5, 4, 3, 2, 1, 0.5 or 0).

The value of y also depends on the serogroup: for serogroup W135, y is 26 or more (e.g. 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100); for serogroup Y, y is 29 or more (e.g. 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100).

The value of z is 27 or less (e.g. 26, 25, 24, 23, 22, 21, 20, 19, 18, 17, 16, 15, 14, 13, 12, 11, 10, 9, 8, 7, 6, 5, 4, 3, 2, 1, 0.5 or 0).

Preferably, x>m, where m is selected from: 0, 0.5, 1, 2, 3, 4, 5, 6, 7, 8, 9 and 10.

Preferably, z>p, where p is selected from: 0, 0.5, 1, 2, 3, 4, 5, 6, 7, 8, 9 and 10.

Saccharides of the Invention

More generally, the invention provides a modified meningococcal capsular saccharide, optionally conjugated to a carrier protein, wherein the saccharide comprises n or more repeating units of the disaccharide unit {[sialic acid]-[hexose]} where the hexose is either galactose or glucose and n is an integer from 1 to 100, and wherein (a) ≤x % of the sialic acid residues in said n or more repeating units are O-acetylated at the 7 position; and/or (b) when hexose is galactose, y % of the sialic acid residues in said n or more repeating units are O-acetylated at the 9 position, and when hexose is glucose, ≥y % or ≤z % of the sialic acid residues in said n or more repeating units are O-acetylated at the 9 position.

The value of x depends on the hexose: when hexose is galactose, x is 29 or less (e.g. 28, 27, 26, 25, 24, 23, 22, 21, 20, 19, 18, 17, 16, 15, 14, 13, 12, 11, 10, 9, 8, 7, 6, 5, 4, 3, 2, 1, 0.5 or 0); when hexose is glucose, x is 9 or less (e.g. 8, 7, 6, 5, 4, 3, 2, 1, 0.5 or 0).

The value of y depends on the hexose: when hexose is galactose, y is 26 or more (e.g. 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100); when hexose is glucose, y is 29 or more (e.g. 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100).

The value of z is 27 or less (e.g. 26, 25, 24, 23, 22, 21, 20, 19, 18, 17, 16, 15, 14, 13, 12, 11, 10, 9, 8, 7, 6, 5, 4, 3, 2, 1, 0.5 or 0).

Preferably, x>m, as defined above. Preferably, z>p, as defined above.

Preferably the sialic acid is N-acetyl neuraminic acid.

When the hexose is galactose, the {[sialic acid]-[hexose]} disaccharide unit is preferably: →4)-D-Neup5Ac(7/9OAc)-α-(2→6)-D-Gal-α-(1→

When the hexose is glucose, the {[sialic acid]-[hexose]} disaccharide unit is preferably: →4)-D-Neup5Ac(7/9OAc)-α-(2→6)-D-Glc-α-(1→

Preferably, the modified meningococcal capsular saccharide is conjugated to a carrier protein. In such conjugates: (i) preferably between 2-9%, more preferably between 4-8%, more preferably between 5-7%, even more preferably about 6% of the sialic acid residues are O-acetylated at the 7 position; (ii) preferably between 35-55%, more preferably between 40-50%, more preferably between 42-46%, even more preferably about 43% (when hexose is Gal) or about 45% (when hexose is Glc) of the sialic acid residues are O-acetylated at the 9 position.

The invention also provides a composition comprising a molecules of serogroup W135 meningococcal capsular saccharide, wherein the average number of sialic acid residues per capsular saccharide molecule is b, and wherein: (a) ≤x % of the a·b serogroup W135 sialic acid residues in the composition are O-acetylated at the 7 position; and/or (b) ≥y % of the a·b serogroup W135 sialic acid residues in the composition are O-acetylated at the 9 position, and wherein x and y are as defined above.

The invention also provides a composition comprising a molecules of serogroup Y meningococcal capsular saccharide, wherein the average number of sialic acid residues per capsular saccharide molecule is b, and wherein: (a) ≤x % of the a·b serogroup Y sialic acid residues in the composition are O-acetylated at the 7 position; and/or (b) ≥y % or ≤z % of the a·b serogroup Y sialic acid residues in the composition are O-acetylated at the 9 position, and wherein x, y and z are as defined above.

The saccharides in said populations may be conjugated to protein carriers and/or be free in solution.

Preferably the saccharides or conjugates of the invention are in a purified form e.g. substantially in the absence of native polysaccharide.

Structural Representations

This invention also provides a saccharide, optionally conjugated to a carrier protein, comprising n or more repeats of the following disaccharide unit:

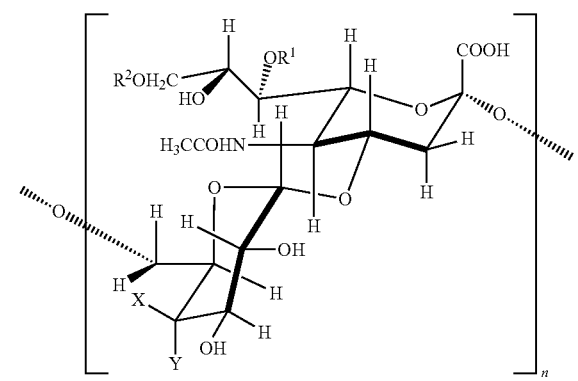

wherein:
n is an integer from 1 to 100,
X and Y are different groups selected from —H and —OH,
$R^1$ is independently selected from —H and —COCH$_3$ and may be the same or different in each disaccharide unit,
$R^2$ is independently selected from —H and —COCH$_3$ and may be the same or different in each disaccharide unit, and when
X is —OH and Y is —H, (a) ≤x % of $R^1$ are —COCH$_3$ and/or (b) ≥y % of $R^2$ are —COCH$_3$.
X is —H and Y is —OH, (a) ≤x % of $R^1$ are —COCH$_3$ and/or (b) ≥y % or ≤z % of $R^2$ are —COCH$_3$.

When X is —OH and Y is —H, x is 29 or less (e.g. 28, 27, 26, 25, 24, 23, 22, 21, 20, 19, 18, 17, 16, 15, 14, 13, 12, 11, 10, 9, 8, 7, 6, 5, 4, 3, 2, 1, 0.5 or 0) and y is 26 or more (e.g. 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100).

When X is —H and Y is —OH, x is 9 or less (e.g. 8, 7, 6, 5, 4, 3, 2, 1 or 0.5), y is 29 or more (e.g. 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100) and z is 27 or less (e.g. 26, 25, 24, 23, 22, 21, 20, 19, 18, 17, 16, 15, 14, 13, 12, 11, 10, 9, 8, 7, 6, 5, 4, 3, 2, 1, 0.5 or 0).

Preferably, x>m, where m is as defined above. Preferably, z>p, where p is as defined above.

Preferably, the saccharide is conjugated to a carrier protein.

When the saccharide is conjugated to a carrier protein and X is —OH and Y is —H: (a) preferably about 2-10%, more preferably about 4-8%, more preferably about 5-7%, even more preferably about 6% of $R^1$ are —COCH$_3$; and/or (b) preferably about 35-55%, more preferably about 40-50%, more preferably about 42-44%, even more preferably about 43% of $R^2$ are —COCH$_3$.

When the saccharide is conjugated to a carrier protein and X is —H and Y is —OH: (a) preferably about 2-9%, more preferably about 4-8%, more preferably about 5-7%, even more preferably about 6% of $R^1$ are —COCH$_3$; and/or (b) preferably about 35-55%, more preferably about 40-50%, more preferably about 42-46%, even more preferably about 45% of $R^2$ are —COCH$_3$.

The O-acetylation status of the sialic acid residues at the 7 and 9 positions in saccharides and conjugates of the invention may be measured using 1D and 2D proton NMR, as described below. HPAEC can be used to measure total O-acetylation, but it cannot distinguish between different positions [234]. Ion spray MS has been used for analysing O-acetylation in MenA [235].

Process for Preparing a Modified Saccharide

The invention also provides a process for preparing an immunogenic conjugate comprising the steps of: (1) providing a starting meningococcal capsular saccharide and a carrier protein, either or both of which is/are optionally modified to render it/them reactive towards the other; (2) forming a covalent bond between the saccharide and the carrier protein; and (3) purifying the resulting glycoconjugates, wherein, between steps (1) and (3) (e.g. during reaction step (2)), the degree of O-acetylation at the 9 position of sialic acid residues in the starting saccharide increases.

The meningococcal capsular saccharide is preferably from serogroup W135 or Y.

Capsular Saccharide Starting Materials

The modified capsular saccharides of the invention are obtainable from the saccharides found in the capsule of *N. meningitidis* serogroups W135 or Y. Saccharides of the invention are thus preferably modified *N. meningitidis* serogroup W135 saccharides and modified *N. meningitidis* serogroup Y saccharides.

Meningococcal capsular polysaccharides are typically prepared by a process comprising the steps of polysaccharide precipitation (e.g. using a cationic detergent), ethanol fractionation, cold phenol extraction (to remove protein) and ultracentrifugation (to remove LPS) [e.g. ref 13].

A more preferred process [14] involves polysaccharide precipitation followed by solubilisation of the precipitated polysaccharide using a lower alcohol. Precipitation can be achieved using a cationic detergent such as tetrabutylammonium and cetyltrimethylammonium salts (e.g. the bromide salts), or hexadimethrine bromide and myristyltrimethylammonium salts. Cetyltrimethylammonium bromide ('CTAB') is particularly preferred [15]. Solubilisation of the precipitated material can be achieved using a lower alcohol such as methanol, propan-1-ol, propan-2-ol, butan-1-ol, butan-2-ol, 2-methyl-propan-1-ol, 2-methyl-propan-2-ol, diols, etc., but ethanol is particularly suitable for solubilising CTAB-polysaccharide complexes. Ethanol is preferably added to the precipitated polysaccharide to give a final concentration (based on total content of ethanol and water) of between 50% and 95%.

After re-solubilisation, the polysaccharide may be further treated to remove contaminants. This is particularly important in situations where even minor contamination is not acceptable (e.g. for human vaccine production). This will typically involve one or more steps of filtration e.g. depth filtration, filtration through activated carbon may be used, size filtration and/or ultrafiltration. Once filtered to remove contaminants, the polysaccharide may be precipitated for further treatment and/or processing. This can be conveniently achieved by exchanging cations (e.g. by the addition of calcium or sodium salts).

Saccharides of the invention may be polysaccharides or oligosaccharides. Oligosaccharides have a degree of polymerisation less than that found in native capsular polysaccharides present in bacteria.

The invention preferably uses oligosaccharides. These preferably have an average degree of polymerisation of less than 30 e.g. between 15 and 25, preferably around 15-20). The degree of polymerisation can conveniently be measured by ion exchange chromatography or by colorimetric assays [16].

Oligosaccharides are conveniently formed by fragmentation of purified capsular polysaccharide (e.g. by hydrolysis, by mild acid treatment, by heating, etc.), which will usually be followed by purification of the fragments of the desired size. If hydrolysis is performed, the hydrolysate will generally be sized in order to remove short-length oligosaccharides. This can be achieved in various ways, such as ultrafiltration followed by ion-exchange chromatography. Oligosaccharides with a degree of polymerisation of less than around 4 are preferably removed for serogroups W135 and Y.

As an alternative to purification from native sources, capsular saccharides (and oligosaccharides in particular) may be obtained by total or partial synthesis e.g. Hib synthesis is disclosed in ref 17, and MenA synthesis in ref 18.

Covalent Conjugation

Modified saccharides of the invention may be subjected to any usual downstream processing which is applied to saccharides (e.g. derivatisation, conjugation, fragmentation, etc.). To enhance immunogenicity, modified saccharides of the invention are preferably conjugated to a carrier protein. Conjugation to carrier proteins is particularly useful for paediatric vaccines [19] and is a well known technique [e.g. reviewed in refs. 20 to 28 etc.].

The invention thus provides a conjugate of a carrier protein and a saccharide of the invention.

Preferred carrier proteins are bacterial toxins or toxoids, such as diphtheria toxoid or tetanus toxoid. The CRM$_{197}$ derivative of diphtheria toxin [29-31] is particularly preferred. Other suitable carrier proteins include the *N. meningitidis* outer membrane protein [32], synthetic peptides [33,34], heat shock proteins [35,36], pertussis proteins [37, 38], cytokines [39], lymphokines [39], hormones [39], growth factors [39], artificial proteins comprising multiple human CD4+ T cell epitopes from various pathogen-derived antigens [40] such as the N19 protein [41], protein D from *H. influenzae* [42,43], pneumococcal surface protein PspA [44], pneumolysin [45], iron-uptake proteins [46], toxin A or B from *C. difficile* [47], mutant bacterial toxins (e.g. cholera toxin 'CT' or *E. coli* heat labile toxin 'LT'), such as a CT with a substitution at Glu-29 [48], etc. Preferred carriers are diphtheria toxoid, tetanus toxoid, *H. influenzae* protein D, and $CRM_{197}$.

Within a composition of the invention, it is possible to use more than one carrier protein e.g. to reduce the risk of carrier suppression. Thus different carrier proteins can be used for different serogroups e.g. serogroup W135 saccharides might be conjugated to $CRM_{197}$ while serogroup Y saccharides might be conjugated to tetanus toxoid. It is also possible to use more than one carrier protein for a particular saccharide antigen e.g. serogroup Y saccharides might be in two groups, with some conjugated to $CRM_{197}$ and others conjugated to tetanus toxoid. In general, however, it is preferred to use the same carrier protein for all serogroups, with $CRM_{197}$ being the preferred choice.

A single carrier protein might carry more than one saccharide antigen [49]. For example, a single carrier protein might have conjugated to it saccharides from serogroups W135 and Y. In general, however, it is preferred to have separate conjugates for each serogroup.

Conjugates with a saccharide:carrier ratio (w/w) of between 1:5 (i.e. excess protein) and 5:1 (i.e. excess saccharide) are preferred. Ratios between 1:2 and 5:1 are preferred, as are ratios between 1:1.25 and 1:2.5 are more preferred. The ratio may be about 1.1, for MenW135 conjugates and 0.7 for MenY conjugates. Based on a 10 µg quantity of MenW135 or MenY saccharide, preferred conjugates comprise from 6.6-20 µg $CRM_{197}$ carrier.

Conjugates may be used in conjunction with free carrier protein [50]. When a given carrier protein is present in both free and conjugated form in a composition of the invention, the unconjugated form is preferably no more than 5% of the total amount of the carrier protein in the composition as a whole, and more preferably present at less than 2% by weight.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [51,52,etc.]). Other suitable techniques use carbodiimides, hydrazides, active esters, norborane, p-nitrobenzoic acid, N-hydroxysuccinimide, S—NHS, EDC, TSTU; see also the introduction to reference 26).

Linkages via a linker group may be made using any known procedure, for example, the procedures described in references 3 and 53. One type of linkage involves reductive amination of the polysaccharide, coupling the resulting amino group with one end of an adipic acid linker group, and then coupling a protein to the other end of the adipic acid linker group [24,54,55]. A preferred type of linkage is a carbonyl linker, which may be formed by reaction of a free hydroxyl group of the modified saccharide with CDI [56, 57] followed by reaction with a protein to form a carbamate linkage. Another preferred type of linkage is an adipic acid linker, which may be formed by coupling a free —$NH_2$ group on the modified saccharide with adipic acid (using, for example, diimide activation), and then coupling a protein to the resulting saccharide-adipic acid intermediate. [24,54, 58]. Another preferred type of linkage may be formed by reaction of a free hydroxyl group of a saccharide with a cyanylating agent (e.g. p-nitrophenylcyanate, 1-cyano-4-(dimethylamino)-pyridinium tetrafluoroborate (CDAP), N-cyanotriethylammonium tetrafluoroborate (CTEA) or), followed by reaction with an amine group on the protein (optionally via a spacer, e.g. a hydrazine) [59,60]. Other linkers include B-propionamido [61], nitrophenyl-ethylamine [62], haloacyl halides [63], glycosidic linkages [2,64], 6-aminocaproic acid [65], ADH [66], $C_4$ to $C_{12}$ moieties [67], etc. As an alternative to using a linker, direct linkage can be used. Direct linkages to the protein may comprise oxidation of the polysaccharide followed by reductive amination with the protein, as described in, for example, references 2 and 68.

Conjugation may involve: reduction of the anomeric terminus to a primary hydroxyl group, optional protection/deprotection of the primary hydroxyl group; reaction of the primary hydroxyl group with CDI to form a CDI carbamate intermediate; and coupling the CDI carbamate intermediate with an amino group on a protein.

A process involving the introduction of amino groups into the saccharide (e.g. by replacing terminal =O groups with —$NH_2$) followed by derivatisation with an adipic diester (e.g. adipic acid N-hydroxysuccinimido diester) and reaction with carrier protein is preferred. Another preferred reaction uses CDAP activation with a protein D carrier.

After conjugation, free and conjugated saccharides can be separated. There are many suitable methods, including hydrophobic chromatography, tangential ultrafiltration, diafiltration etc. [see also refs. 69 & 70, etc.].

Where the composition of the invention includes a conjugated oligosaccharide, it is preferred that oligosaccharide preparation precedes conjugation.

Pharmaceutical Compositions

The invention provides an immunogenic composition (e.g. a vaccine) comprising (a) a modified capsular saccharide of the invention and/or a conjugate of the invention, and (b) a pharmaceutically acceptable carrier. Vaccines based on saccharides or saccharide-protein conjugates are well known in the art, including conjugates based on de-O-acetylated saccharides (NeisVac-C™). Vaccines of the invention may either be prophylactic (i.e. to prevent infection) or therapeutic (i.e. to treat infection), but will typically be prophylactic.

'Pharmaceutically acceptable carriers' include any carrier that does not itself induce the production of antibodies harmful to the individual receiving the pharmaceutical composition. Suitable carriers are typically large, slowly metabolised macromolecules such as proteins, polysaccharides, polylactic acids, polyglycolic acids, polymeric amino acids, amino acid copolymers, trehalose [71] lipid aggregates (such as oil droplets or liposomes), and inactive virus particles. Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. A thorough discussion of pharmaceutically acceptable excipients is available in reference 72.

Typically, the pharmaceutical compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. Direct delivery of the pharmaceutical compositions will generally be parenteral (e.g. by injection, either subcutaneously, intraperitoneally, intravenously or intramuscularly, or delivered to the interstitial space of a tissue). The pharmaceutical compositions can also be administered into a lesion. Other modes of administration include oral and pulmonary administration, rectal (suppositories), and transdermal or transcutaneous applications [e.g. ref 73], needles, and hyposprays.

The pH of the composition is preferably between 6 and 8, preferably about 7. Stable pH may be maintained by the use of a buffer. Where a composition comprises an aluminium hydroxide salt, it is preferred to use a histidine buffer [74]. The composition may be sterile and/or pyrogen-free. Compositions of the invention may be isotonic with respect to humans.

Compositions of the invention may be in aqueous form (i.e. solutions or suspensions) or in dry form (e.g. lyophilised powders). Liquid formulation allow the compositions to be administered direct from their packaged form, without the need for reconstitution in an aqueous medium, and are thus ideal for injection. Such compositions may be presented in vials, or they may be presented in ready-filled syringes. The syringes may be supplied with or without needles. A syringe will include a single dose of the composition, whereas a vial may include a single dose or multiple doses.

Liquid compositions of the invention are also suitable for reconstituting other vaccines from a lyophilised form e.g. to reconstitute lyophilised Hib or DTP antigens. Where a composition of the invention is to be used for such extemporaneous reconstitution, the invention provides a kit, which may comprise two vials, or may comprise one ready-filled syringe and one vial, with the contents of the syringe being used to reactivate the contents of the vial prior to injection.

Dry compositions of the invention offer storage stability, but must be reconstituted into liquid form prior to administration. The invention provides a kit comprising a first container containing a dry composition of the invention and a second container containing an aqueous composition for reconstituting the contents of the first container. The aqueous composition in the second container may contain antigens (e.g. non-meningococcal), or may contain only excipients. The first container will generally be a vial; the second container may also be a vial, or it may be a ready-filled syringe.

For preparing dry compositions, stabilisers may be used e.g. disaccharides such as trehalose and sucrose, or sugar alcohols such as mannitol. These components will be added prior to lyophilisation and will appear in the reconstituted composition.

Further components of compositions include: sodium chloride (for tonicity), e.g. at about 9 mg/ml; detergent e.g. a Tween (polysorbate), such as Tween 80, generally at low levels e.g. <0.01%; and buffer salts e.g. a phosphate buffer. The composition may include an antibiotic agent.

Compositions of the invention may be packaged in unit dose form or in multiple dose form. For liquid multiple dose forms, vials are preferred to pre-filled syringes. Effective doses can be routinely established, but a typical human dose of the composition for injection has a volume of 0.5 ml.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

A typical quantity of each meningococcal saccharide antigen per dose is between 1 µg and 20 µg e.g. about 1 µg, about 2.5 µg, about 4 µg, about 5 µg, or about 10 µg (expressed as saccharide).

Each saccharide may be present at substantially the same quantity per dose. However, an excess of MenY saccharide may be preferred e.g. a MenY:MenW135 ratio (w/w) of 1.5:1 or more.

Where a conjugate is present, a composition may also comprise free carrier protein [50]. Preferably, the free carrier protein is present at less than 5% by weight of the composition; more preferably, it is present at less than 2% by weight.

Compositions of the invention will generally include one or more adjuvants. Such adjuvants include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 75], or mixtures of different mineral compounds, with the compounds taking any suitable form (e.g. gel, crystalline, amorphous, etc.), and with adsorption being preferred. The mineral containing compositions may also be formulated as a particle of metal salt [76].

B. Oil Emulsions

Oil emulsion compositions suitable for use as adjuvants in the invention include squalene-water emulsions, such as MF59 [Chapter 10 of ref 75; see also ref 77] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. Saponin Formulations [Chapter 22 of Ref. 75]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref 78. Saponin formulations may also comprise a sterol, such as cholesterol [79].

Combinations of saponins and cholesterols can be used to form unique particles called immunostimulating complexes (ISCOMs) [chapter 23 of ref 75]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 79-81. Optionally, the ISCOMS may be devoid of additional detergent [82].

A review of the development of saponin based adjuvants can be found in refs. 83 & 84.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 85-90. Virosomes are discussed further in, for example, ref 91

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref 92. Such "small particles" of 3dMPL are small enough to be sterile filtered through a 0.22 µm membrane [92]. Other non-toxic LPS derivatives include monophosphoryl lipid A mimics, such as aminoalkyl glucosaminide phosphate derivatives e.g. RC-529 [93,94].

Lipid A derivatives include derivatives of lipid A from *Escherichia coli* such as OM-174. OM-174 is described for example in refs. 95 & 96.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 97, 98 and 99 disclose possible analog substitutions e.g. replacement of guanosine with 2'-deoxy-7-deazaguanosine. The adjuvant effect of CpG oligonucleotides is further discussed in refs. 100-105.

The CpG sequence may be directed to TLR9, such as the motif GTCGTT or TTCGTT [106]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 107-109. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 106 & 110-112.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 113 and as parenteral adjuvants in ref 114. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 115-122. Numerical reference for amino acid substitutions is preferably based on the alignments of the A and B subunits of ADP-ribosylating toxins set forth in ref 123, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12, etc.) [124], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [125] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [126].

H. Microparticles

Microparticles may also be used as adjuvants in the invention. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref 75)

Examples of liposome formulations suitable for use as adjuvants are described in refs. 127-129.

J. Polyoxyethylene Ether and Polyoxyethylene Ester Formulations

Adjuvants suitable for use in the invention include polyoxyethylene ethers and polyoxyethylene esters [130]. Such formulations further include polyoxyethylene sorbitan ester surfactants in combination with an octoxynol [131] as well as polyoxyethylene alkyl ethers or ester surfactants in combination with at least one additional non-ionic surfactant such as an octoxynol [132]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 133 and 134.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 135 and 136.

The invention may also comprise combinations of aspects of one or more of the adjuvants identified above. For example, the following adjuvant compositions may be used in the invention: (1) a saponin and an oil-in-water emulsion [137]; (2) a saponin (e.g. QS21)+a non-toxic LPS derivative (e.g. 3dMPL) [138]; (3) a saponin (e.g. QS21)+a non-toxic LPS derivative (e.g. 3dMPL)+a cholesterol; (4) a saponin (e.g. QS21)+3dMPL+IL-12 (optionally +a sterol) [139]; (5) combinations of 3dMPL with, for example, QS21 and/or oil-in-water emulsions [140]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref 75.

Aluminium salts and calcium phosphate are preferred parenteral adjuvants. Mutant toxins are preferred mucosal adjuvants.

Compositions of the invention that include an aluminium phosphate adjuvant are preferred. Aluminium hydroxide is preferably absent. Aluminium phosphate adjuvant may be included at about 0.6 mg $Al^{3+}$ per ml.

Combinations of Immunogens

Compositions of the invention may comprise both a modified serogroup W135 meningococcal capsular saccharide of the invention and a modified serogroup Y meningococcal capsular saccharide of the invention.

Other antigens may also be included in compositions of the invention. Thus the invention provides a composition comprising a modified serogroup W135 meningococcal capsular saccharide of the invention and/or a modified serogroup Y meningococcal capsular saccharide of the invention, and further comprising one or more antigen(s) selected from the following list:

- a capsular saccharide antigen from serogroup A of *N. meningitidis*.
- a capsular saccharide antigen from serogroup C of *N. meningitidis*.
- a protein antigen from *N. meningitidis* serogroup B, such as those in refs. 141 to 150.

preparations of *N. meningitidis* serogroup B microvesicles [151], 'native OMVs' [152], blebs or outer membrane vesicles [e.g. refs. 153 to 158 etc.]. These may be prepared from bacteria which have been genetically manipulated [159-162] e.g. to increase immunogenicity (e.g. hyper-express immunogens), to reduce toxicity, to inhibit capsular polysaccharide synthesis, to down-regulate PorA expression, etc. They may be prepared from hyperblebbing strains [163-166]. Vesicles from a non-pathogenic *Neisseria* may be included [167]. OMVs may be prepared without the use of detergents [168,169]. They may express non-Neisserial proteins on their surface [170]. They may be LPS-depleted. They may be mixed with recombinant antigens [153, 171]. Vesicles from bacteria with different class I outer membrane protein subtypes may be used e.g. six different subtypes [172,173] using two different genetically-engineered vesicle populations each displaying three subtypes, or nine different subtypes using three different genetically-engineered vesicle populations each displaying three subtypes, etc. Useful subtypes include: P1.7,16; P1.5-1, 2-2; P1,19,15-1; P1.5-2,10; P1.12-1,13; P1.7-2,4; P1.22,14; P1.7-1,1; P1.18-1,3,6.

a saccharide antigen from *Haemophilus influenzae* B [e.g. 174].

an antigen from *Streptococcus pneumoniae* [e.g. 208, 209, 210].

an antigen from hepatitis A virus, such as inactivated virus [e.g. 175, 176].

an antigen from hepatitis B virus, such as the surface and/or core antigens [e.g. 176, 177].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 178 & 179]. Cellular pertussis antigens may be used.

a diphtheria antigen, such as a diphtheria toxoid [e.g. chapter 3 of ref 180] e.g. the $CRM_{197}$ mutant [e.g. 181].

a tetanus antigen, such as a tetanus toxoid [e.g. chapter 4 of ref. 180].

polio antigen(s) [e.g. 182, 183], such as IPV.

Toxic protein antigens may be detoxified where necessary (e.g. detoxification of pertussis toxin by chemical and/or genetic means [179]).

Where a diphtheria antigen is included in the pharmaceutical composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens in the pharmaceutical composition will typically be present at a concentration of at least 1 μg/ml each. In general, the concentration of any given antigen will be sufficient to elicit an immune response against that antigen.

Antigens are preferably adsorbed to an aluminium salt adjuvant.

As an alternative to using proteins antigens in the pharmaceutical composition of the invention, nucleic acid encoding the antigen may be used [e.g. refs. 184 to 192]. Protein components of the pharmaceutical compositions of the invention may thus be replaced by nucleic acid (preferably DNA e.g. in the form of a plasmid) that encodes the protein. Similarly, compositions of the invention may comprise proteins which mimic saccharide antigens e.g. mimotopes [193] or anti-idiotype antibodies. These may replace individual saccharine components, or may supplement them.

As an example, the vaccine may comprise a peptide mimic of the MenC [194] or the MenA [195] capsular polysaccharide in place of the saccharide itself.

Combined Meningococcus Vaccines

Preferred compositions of the invention comprise a modified serogroup W135 meningococcal capsular saccharide of the invention, a modified serogroup Y meningococcal capsular saccharide of the invention, and a serogroup C capsular saccharide, wherein the capsular saccharides are conjugated to carrier proteins. The composition may also include a serogroup A capsular saccharide, preferably conjugated to a carrier protein. The saccharides in these compositions are preferably oligosaccharides. Oligosaccharide conjugates can be prepared as disclosed in reference 14.

Serogroup A saccharides may be O-acetylated or de-O-acetylated. Serogroup C saccharides may be O-acetylated or de-O-acetylated.

Preferred MenC conjugates include, based on 10 μg saccharide, 12.5-25 μg $CRM_{197}$ carrier. Preferred MenA conjugates include, based on 10 μg saccharide, 12.5-33 μg $CRM_{197}$ carrier.

Typical doses for MenC and MenA conjugates are the same as for MenW135 and MenY i.e. between 1 μg and 20 μg e.g. about 1 μg, about 2.5n, about 4 μg, about 5 μg, or about 10 μg.

Preferred ratios (w/w) for saccharides from serogroups C:W135:Y are: 1:1:1; 1:1:2; 1:1:1; 2:1:1; 4:2:1; 2:1:2; 4:1:2; 2:2:1; and 2:1:1. Preferred ratios for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1. Using a substantially equal mass of each saccharide per dose is preferred.

Where a composition includes a serogroup A saccharide, it may be prepared by reconstituting the serogroup A saccharide from a lyophilised form, using an aqueous composition that comprises one or more of the serogroup C, W135 and/or Y saccharides.

Where a composition includes a serogroup A saccharide, it may be a modified saccharide in which one or more of the hydroxyl groups on the native saccharide has/have been replaced by a blocking group [196]. This modification improves resistance to hydrolysis. It is preferred that all or substantially all the monosaccharide units may have blocking group substitutions.

As well as including saccharide antigens from serogroups Y, W135 and C (and, optionally, A), compositions of the invention may include one or more antigens from serogroup B. Unlike serogroups A, C, W135 and Y, the capsular saccharide of MenB is unsuitable for use as an immunogen in humans because of its similarity to self antigens. If a saccharide antigen is to be used for MenB, therefore, it is necessary to use a modified saccharide, such as one in which N-acetyl groups in the saccharide's sialic acid residues are replaced with N-acyl groups. Suitable N-acyl groups are $C_1$ to $C_8$ acyl groups, such as N-propionyl [197]. Rather than use a saccharide antigen, however, it is preferred to use a polypeptide antigen.

Thus the composition may include one or more polypeptide antigens which induce(s) an immune response that protects against MenB infection. More generally, the composition can, after administration to a subject, induce an antibody response in the subject that is bactericidal against two or more (e.g. 2 or 3) of hypervirulent lineages A4, ET-5 and lineage 3 of *N. meningitidis* serogroup B.

The genome sequence of serogroup B *N. meningitidis* has been published [148] and suitable antigens can be selected from the encoded polypeptides [150]. Examples of antigens are disclosed in references 141 to 150. Preferred compositions include one or more of the following five antigens [198]: (1) a 'NadA' protein, preferably in oligomeric form (e.g. in trimeric form); (2) a '741' protein; (3) a '936' protein; (4) a '953' protein; and (5) a '287' protein.

Prototype sequences for these five proteins are found in reference 143 as follows:

| | Protein | | | | |
|---|---|---|---|---|---|
| | NadA | 741 | 936 | 953 | 287 |
| SEQ ID NOS | 2943 & 2944 | 2535 & 2536 | 2883 & 2884 | 2917 & 2918 | 3103 & 3104 |

When used in compositions of the invention, the serogroup B protein may comprise the amino acid sequence of one of these prototype sequences, or it may comprise an amino acid sequence which: (a) has 50% or more identity (e.g. 60%, 70%, 80%, 90%, 95%, 99% or more) to the prototype sequence; and/or (b) comprises a fragment of at least n consecutive amino acids of the prototype sequence, where n is 7 or more (eg. 8, 10, 12, 14, 16, 18, 20, 25, 30, 35, 40, 50, 60, 70, 80, 90, 100, 150, 200, 250 or more). Preferred fragments for (b) lack one or more amino acids (e.g. 1, 2, 3, 4, 5, 6, 7, 8, 9, 10, 15, 20, 25 or more) from the C-terminus and/or the N-terminus of the prototype sequence. Other preferred fragments comprise an epitope from the sequence.

These five MenB antigens may be present in the composition as five separate proteins, but it is preferred that at least two of the antigens are expressed as a single polypeptide chain (a 'hybrid' protein [refs. 145-147]) i.e. such that the five antigens form fewer than five polypeptides. Hybrid proteins offer two principal advantages: first, a protein that may be unstable or poorly expressed on its own can be assisted by adding a suitable hybrid partner that overcomes the problem; second, commercial manufacture is simplified as only one expression and purification need be employed in order to produce two separately-useful proteins. A hybrid protein included in a composition of the invention may comprise two or more (i.e. 2, 3, 4 or 5) of the five basic antigens. Hybrids consisting of two of the five antigens are preferred e.g. those comprising: NadA & 741; NadA & 936; NadA & 953; NadA & 287; 741 & 936; 741 & 953; 741 & 287; 936 & 953; 936 & 287; 953 & 287.

Three preferred MenB antigens for combined inclusion in compositions of the invention are:

```
NadA from strain 2996, with C-terminus deletion and leader peptide processed
ATNDDDVKKAATVAIAAAYNNGQEINGFKAGETIYDIDEDGTITKKDATAADVEADDFKGLGLKKVVTNLTKTVNENKQN

VDAKVKAAESEIEKLTTKLADTDAALADTDAALDATTNALNKLGENITTFAEETKTNIVKIDEKLEAVADTVDKHAEAFN

DIADSLDETNTKADEAVKTANEAKQTAEETKQNVDAKVKAAETAAGKAEAAAGTANTAADKAEAVAAKVTDIKADIATNK
```

```
DNIAKKANSADVYTREESDSKFVRIDGLNATTEKLDTRLASAEKSIADHDTRLNGLDKTVSDLRKETRQGLAEQAALSGL

FQPYNVG 287-953 hybrid
MASPDVKSADTLSKPAAPVVSEKETEAKEDAPQAGSQGQGAPSAQGGQDMAAVSEENTGNGGAAATDKPKNEDEGAQNDM

PQNAADTDSLTPNHTPASNMPAGNMENQAPDAGESEQPANQPDMANTADGMQGDDPSAGGENAGNTAAQGTNQAENNQTA

GSQNPASSTNPSATNSGGDFGRTNVGNSVVIDGPSQNITLTHCKGDSCSGNNFLDEEVQLKSEFEKLSDADKISNYKKDG

KNDGKNDKFVGLVADSVQMKGINQYIIFYKPKPTSFARFRRSARSRRSLPAEMPLIPVNQADTLIVDGEAVSLTGHSGNI

FAPEGNYRYLTYGAEKLPGGSYALRVQGEPSKGEMLAGTAVYNGEVLHFHTENGRPSPSRGRFAAKVDFGSKSVDGIIDS

GDGLHMGTQKFKAAIDGNGFKGTWTENGGGDVSGKFYGPAGEEVAGKYSYRPTDAEKGGFGVFAGKKEQDGSGGGGATYK

VDEYHANARFAIDHENTSTNVGGFYGLTGSVEFDQAKRDGKIDITIPVANLQSGSQHFTDHLKSADIFDAAQYPDIRFVS

TKENENGKKLVSVDGNLTMHGKTAPVKLKAEKENCYQSPMAKTEVCGGDFSTTIDRTKWGVDYLVNVGMTKSVRIDIQIE

AAKQ*

936-741 hybrid
MVSAVIGSAAVGAKSAVDRRTTGAQTDDNVMALRIETTARSYLRQNNQTKGYTPQISVVGYNRHLLLLGQVATEGEKQFV

GQIARSEQAAEGVYNYITVASLPRTAGDIAGDTWNTSKVRATLLGISPATQARVKIVTYGNVTYVMGILTPEEQAQITQK

VSTTVGVQKVITLYQNYVQRGSGGGGVAADIGAGLADALTAPLDHKDKGLQSLTLDQSVRKNEKLKLAAQGAEKTYGNGD

SLNTGKLKNDKVSRFDFIRQIEVDGQLITLESGEFQVYKQSHSALTAFQTEQIQDSEHSGKMVAKRQFRIGDIAGEHTSF

DKLPEGGRATYRGTAFGSDDAGGKLTYTIDFAAKQGNGKIEHLKSPELNVDLAAADIKPDGKRHAVISGSVLYNQAEKGS

YSLGIFGGKAQEVAGSAEVKTVNGIRHIGLAAKQ*
```

As mentioned above, compositions of the invention that include MenB antigens can preferably induce a serum bactericidal antibody response that is effective against two or three of MenB hypervirulent lineages A4, ET-5 and lineage 3. They may additionally induce bactericidal antibody responses against one or more of hypervirulent lineages subgroup I, subgroup III, subgroup IV-1 or ET-37 complex, and against other lineages e.g. hyperinvasive lineages. These antibody responses are conveniently measured in mice and are a standard indicator of vaccine efficacy [e.g. see end-note 14 of reference 150]. The composition need not induce bactericidal antibodies against each and every MenB strain within these hypervirulent lineages; rather, for any given group of four of more strains of serogroup B meningococcus within a particular hypervirulent lineage, the antibodies induced by the composition are bactericidal against at least 50% (e.g. 60%, 70%, 80%, 90% or more) of the group. Preferred groups of strains will include strains isolated in at least four of the following countries: GB, AU, CA, NO, IT, US, NZ, NL, BR, and CU. The serum preferably has a bactericidal titre of at least 1024 (e.g. $2^{10}$, $2^{11}$, $2^{12}$, $2^{13}$, $2^{14}$, $2^{15}$, $2^{16}$, $2^{17}$, $2^{18}$ or higher, preferably at least $2^{14}$) i.e. the serum is able to kill at least 50% of test bacteria of a particular strain when diluted 1/1024, as described in reference 150. Preferred compositions can induce bactericidal responses against the following strains of serogroup B meningococcus: (i) from cluster A4, strain 961-5945 (B:2b: P1.21,16) and/or strain G2136 (B:-); (ii) from ET-5 complex, strain MC58 (B:15:P1.7,16b) and/or strain 44/76 (B:15:P1.7,16); (iii) from lineage 3, strain 394/98 (B:4:P1.4) and/or strain BZ198 (B:NT:-). More preferred compositions can induce bactericidal responses against strains 961-5945, 44/76 and 394/98. Strains 961-5945 and G2136 are both Neisseria MLST reference strains [ids 638 & 1002 in ref. 199]. Strain MC58 is widely available (e.g. ATCC BAA-335) and was the strain sequenced in reference 148. Strain 44/76 has been widely used and characterised (e.g. ref 200) and is one of the Neisseria MLST reference strains [id 237 in ref 199; row 32 of Table 2 in ref 201]. Strain 394/98 was originally isolated in New Zealand in 1998, and there have been several published studies using this strain (e.g. refs. 202 & 203). Strain BZ198 is another MLST reference strain [id 409 in ref. 199; row 41 of Table 2 in ref. 201]. The composition may additionally induce a bactericidal response against serogroup W135 strain LNP17592 (W135:2a:P1.5, 2), from ET-37 complex. This is a Haji strain isolated in France in 2000.

Other MenB polypeptide antigens which may be included in compositions of the invention include those comprising one of the following amino acid sequences: SEQ ID NO:650 from ref. 141; SEQ ID NO:878 from ref. 141; SEQ ID NO:884 from ref. 141; SEQ ID NO:4 from ref. 142; SEQ ID NO:598 from ref. 143; SEQ ID NO:818 from ref. 143; SEQ ID NO:864 from ref. 143; SEQ ID NO:866 from ref. 143; SEQ ID NO:1196 from ref. 143; SEQ ID NO:1272 from ref. 143; SEQ ID NO:1274 from ref. 143; SEQ ID NO:1640 from ref. 143; SEQ ID NO:1788 from ref. 143; SEQ ID NO:2288 from ref. 143; SEQ ID NO:2466 from ref. 143; SEQ ID NO:2554 from ref. 143; SEQ ID NO:2576 from ref. 143; SEQ ID NO:2606 from ref. 143; SEQ ID NO:2608 from ref. 143; SEQ ID NO:2616 from ref. 143; SEQ ID NO:2668 from ref. 143; SEQ ID NO:2780 from ref. 143; SEQ ID NO:2932 from ref. 143; SEQ ID NO:2958 from ref. 143; SEQ ID NO:2970 from ref. 143; SEQ ID NO:2988 from ref. 143, or a polypeptide comprising an amino acid sequence which: (a) has 50% or more identity (e.g. 60%, 70%, 80%, 90%, 95%, 99% or more) to said sequences; and/or (b) comprises a fragment of at least n consecutive amino acids from said sequences, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from the relevant sequence. More than one (e.g. 2, 3, 4, 5, 6) of these polypeptides may be included.
Combinations with Hib Saccharides Where the composition includes a *H. influenzae* type B antigen, it will typically be a Hib capsular saccharide antigen. Saccharide antigens from *H. influenzae* b are well known.

Advantageously, the Hib saccharide is covalently conjugated to a carrier protein, in order to enhance its immunogenicity, especially in children. The preparation of polysaccharide conjugates in general, and of the Hib capsular polysaccharide in particular, is well documented. The invention may use any suitable Hib conjugate. Suitable carrier proteins are described above, and preferred carriers for Hib saccharides are $CRM_{197}$ ('HbOC'), tetanus toxoid ('PRP-T') and the outer membrane complex of *N. meningitidis* ('PRP-OMP').

The saccharide moiety of the conjugate may be a polysaccharide (e.g. full-length polyribosylribitol phosphate (PRP)), but it is preferred to hydrolyse polysaccharides to form oligosaccharides (e.g. MW from ~1 to ~5 kDa).

A preferred conjugate comprises a Hib oligosaccharide covalently linked to $CRM_{197}$ via an adipic acid linker [16,204]. Tetanus toxoid is also a preferred carrier.

Administration of the Hib antigen preferably results in an anti-PRP antibody concentration of ≥0.15 μg/ml, and more preferably ≥1 μg/ml.

Where a composition includes a Hib saccharide antigen, it is preferred that it does not also include an aluminium hydroxide adjuvant. If the composition includes an aluminium phosphate adjuvant then the Hib antigen may be adsorbed to the adjuvant [205] or it may be non-adsorbed [206]. Prevention of adsorption can be achieved by selecting the correct pH during antigen/adjuvant mixing, an adjuvant with an appropriate point of zero charge, and an appropriate order of mixing for the various different antigens in a composition [207].

Compositions of the invention may comprise more than one Hib antigen. Hib antigens may be lyophilised e.g. for reconstitution by meningococcal compositions of the invention.
Combinations with Pneumococcal Antigens Where the composition includes a *S. pneumoniae* antigen, it will typically be a capsular saccharide antigen which is preferably conjugated to a carrier protein [e.g. refs. 208 to 210]. It is preferred to include saccharides from more than one serotype of *S. pneumoniae*. For example, mixtures of polysaccharides from 23 different serotype are widely used, as are conjugate vaccines with polysaccharides from between 5 and 11 different serotypes [211]. For example, PrevNar™ [212] contains antigens from seven serotypes (4, 6B, 9V, 14, 18C, 19F, and 23F) with each saccharide individually conjugated to $CRM_{197}$ by reductive amination, with 2 μg of each saccharide per 0.5 ml dose (4 μg of serotype 6B), and with conjugates adsorbed on an aluminium phosphate adjuvant. Compositions of the invention preferably include at least serotypes 6B, 14, 19F and 23F. Conjugates may be adsorbed onto an aluminium phosphate.

As an alternative to using saccharide antigens from pneumococcus, the composition may include one or more polypeptide antigens. Genome sequences for several strains of pneumococcus are available [213,214] and can be subjected to reverse vaccinology [215-218] to identify suitable polypeptide antigens [219,220]. For example, the composition may include one or more of the following antigens: PhtA, PhtD, PhtB, PhtE, SpsA, LytB, LytC, LytA, Sp125, Sp101, Sp128, Sp130 and Sp130, as defined in reference 221. The composition may include more than one (e.g. 2, 3, 4, 5, 6, 7, 8, 9 10, 11, 12, 13 or 14) of these antigens.

In some embodiments, the composition may include both saccharide and polypeptide antigens from pneumococcus. These may be used in simple admixture, or the pneumococcal saccharide antigen may be conjugated to a pneumococcal protein. Suitable carrier proteins for such embodiments include the antigens listed in the previous paragraph [221].

Pneumococcal antigens may be lyophilised e.g. together with Hib antigen.
Methods of Treatment The invention also provides a method for raising an antibody response in a mammal, comprising administering a pharmaceutical composition of the invention to the mammal.

The invention provides a method for raising an immune response in a mammal comprising the step of administering an effective amount of a composition of the invention. The immune response is preferably protective and preferably involves antibodies. The method may raise a booster response.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc.

The invention also provides a composition of the invention for use as a medicament. The medicament is preferably able to raise an immune response in a mammal (i.e. it is an immunogenic composition) and is more preferably a vaccine.

The invention also provides the use of a modified serogroup W135 meningococcal capsular saccharide of the invention and/or a modified serogroup Y meningococcal capsular saccharide of the invention in the manufacture of a medicament for raising an immune response in a mammal. The saccharides are preferably conjugated. The medicament is preferably a vaccine.

These uses and methods are preferably for the prevention and/or treatment of a disease caused by a *Neisseria* (e.g. meningitis, septicaemia, bacteremia, gonorrhoea, etc.). The prevention and/or treatment of bacterial and/or meningococcal meningitis is preferred.

One way of checking efficacy of therapeutic treatment involves monitoring Neisserial infection after administration of the composition of the invention. One way of checking efficacy of prophylactic treatment involves monitoring immune responses against the five basic antigens after administration of the composition. Immunogenicity of compositions of the invention can be determined by administering them to test subjects (e.g. children 12-16 months age, or animal models [222]) and then determining standard parameters including serum bactericidal activity (SBA) and ELISA titres (GMT) of total and high-avidity anti-capsule IgG. These immune responses will generally be determined around 4 weeks after administration of the composition, and compared to values determined before administration of the composition. SBA measures bacterial killing mediated by complement, and can be assayed using human or baby rabbit complement. WHO standards require a vaccine to induce at least a 4-fold rise in SBA in more than 90% of recipients. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Neisserial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 223 & 224]. Success with nasal administration of pneumococcal saccharides [225,226], pneumococcal polypeptides [227], Hib saccharides [228], MenC saccharides [229], and mixtures of Hib and MenC saccharide conjugates [230] has been reported.

General

The term "comprising" means "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x+10%.

Expressions such as "≤x % of the sialic acid residues are O-acetylated at the 7 position", do not mean that each saccharide molecule in a composition must necessarily have the same degree of O-acetylation at the 7 position. Nor does it mean that each saccharide molecule in a composition must necessarily have ≤x % O-acetylation at the 7 position. Rather, some may have >x % while others have <x %, but the average degree of acetylation across all of the 7 positions of all the sialic acid residues in the total population of saccharides is ≤x %. The same applies to expressions like "≥y % of the sialic acid residues are O-acetylated at the 9 position" and similar.

It will be appreciated that sugar rings can exist in open and closed form and that, whilst closed forms are shown in structural formulae herein, open forms are also encompassed by the invention.

Sialic acid is also known as neuraminic acid.

MODES FOR CARRYING OUT THE INVENTION

Figure 1:
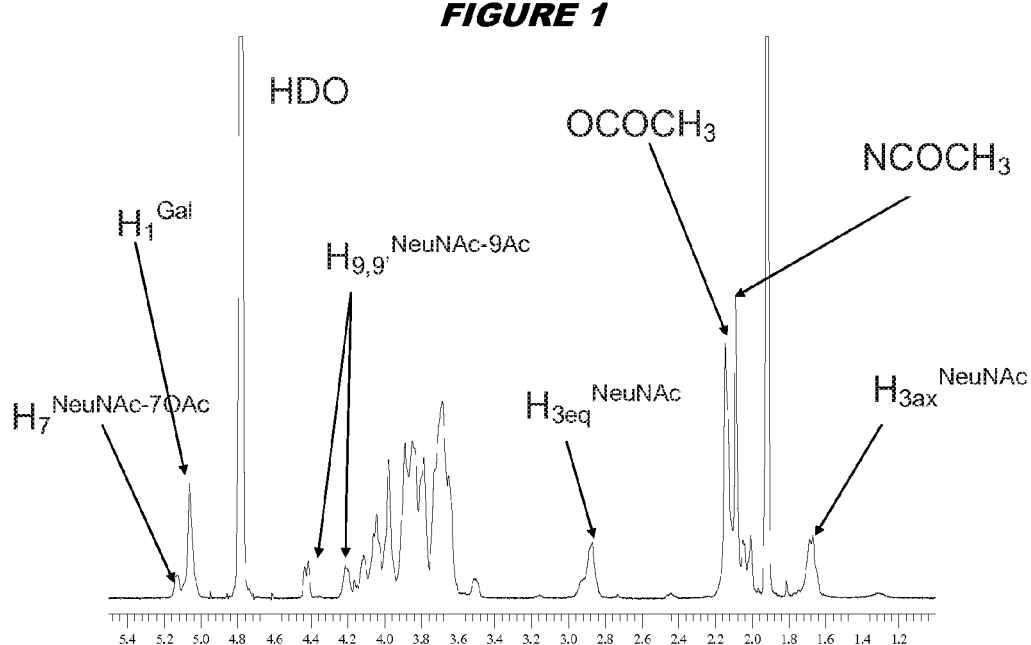
FIGS. 1 and 2 show annotated NMR spectra of hydrolysed MenW135 and MenY, respectively.

A. Production and Purification of Meningococcal Polysaccharides

Capsular polysaccharides were purified from MenW135 and MenY as described in ref. 14.

B. Preparation of Modified Serogroup W135 and Y Polysaccharides Conjugates

The purified polysaccharides were hydrolysed in acetic 50 mM sodium acetate buffer, pH 4.7 for about 3 hours at 80° C. This resulted in oligosaccharides with an average DP of about 15 to 20 as determined by ratio between sialic acid (SA) and reduced terminal SA.

The hydrolysate was ultrafiltered through a 30 kDa cut-off membrane (12 to 20 diafiltration volumes of 5 mM acetate buffer/15-30 mM NaCl pH 6.5). The retentate, containing the high MW species, was discarded while the permeate was loaded onto a Q-Sepharose Fast Flow column equilibrated in 5 mM acetate buffer/15 mM NaCl pH 6.5. The column was then washed with 10 CV equilibrating buffer, in order to remove oligosaccharides with DP≤3-4 and eluted with 3 CV 5 mM acetate buffer/500 mM NaCl pH 6.5.

Ammonium chloride or ammonium acetate was added to the sized oligosaccharide solution to a final concentration of 300 g/L, then sodium-cyano-borohydride was added to 49 g/L or 73 g/L final concentration. The mixture was incubated at 50° C. for 3 days to produce amino-oligosaccharides, which were then purified by tangential flow ultrafiltration with a 1 kDa or 3 kDa cut-off membrane using 13 diafiltration volumes of 0.5 M NaCl followed by 7 diafiltration volumes of 20 mM NaCl. The purified oligosaccharides were then dried with rotary evaporator to remove water.

Dried amino-oligosaccharides were solubilised in distilled water at a 40 mM amino group concentration, then 9 volumes of DMSO were added followed by triethyl-amine at a final concentration of 200 mM. To the resulting solution, adipic acid N-hydroxysuccinimido diester was added for a final concentration of 480 mM. The reaction was maintained under stirring at room temperature for 2 hours, then the activated oligosaccharide was precipitated with acetone (80% v/v final concentration). The precipitate was collected by centrifugation and washed several times with acetone to remove unreacted adipic acid N-hydroxysuccinimido diester and by-products. Finally the activated oligosaccharide was dried under vacuum. The amount of active ester groups introduced into the oligosaccharide structure was determined by a colorimetric method as described in ref. 231.

The dried activated oligosaccharide was added to a 45 mg/ml solution of $CRM_{197}$ in 0.01M phosphate buffer pH 7.2 for an active ester/protein (mole/mole) ratio of 12:1. The reaction was maintained under stirring at room temperature overnight. After this period, the conjugate was purified by diafiltration with a 30 kDa membrane (50 diafiltration volumes of 10 mM phosphate buffer, pH 7.2). The purified conjugate was sterile filtered and stored at −20° C. or −60° C. until vaccine formulation.

C. O-Acetylation Status of Polysaccharides During Conjugation

O-acetylation status of the C7 and C9 positions of the sialic acid residues in the population of modified saccharides derived from MenW135 and Men Y was measured by NMR analysis.

The intermediate poly- and oligo-saccharides of the conjugation process (native polysaccharide, after hydrolysis, prior to amination, after activation and after conjugation) were characterised using 1D and 2D proton NMR experiments. $^1$H NMR samples were prepared by dissolving lyophilized oligosaccharides in 0.75 mL of 99.9% deuterated $^2H_2O$ (Aldrich™) to give 10-15 mM concentrated solutions. In all experiments, 5 mm Wilmad NMR tubes were used.

$^1$H NMR spectra were recorded at 298 K on a Bruker NMR Spectrometer Avance DRX 600 MHz equipped with a BGU unit and using standard Bruker pulse programs. A 5 mm TBI triple resonance probe with self shielded z-gradients was used. For processing data the Bruker XWINNMR 3.0 software was used.

Proton standard spectral acquisition conditions are to collect 32 k data points over a spectral window of 6000 Hz with 4 scans. $^1$H NMR spectra were Fourier-transformed after applying a 0.1 Hz line broadening function and referenced relative to the mono-deuterated water (HDO) at 4.72 ppm.

The assignment of the resonances and hence determination of molecular structure were made based on literature data [232,4].

Figure 2:
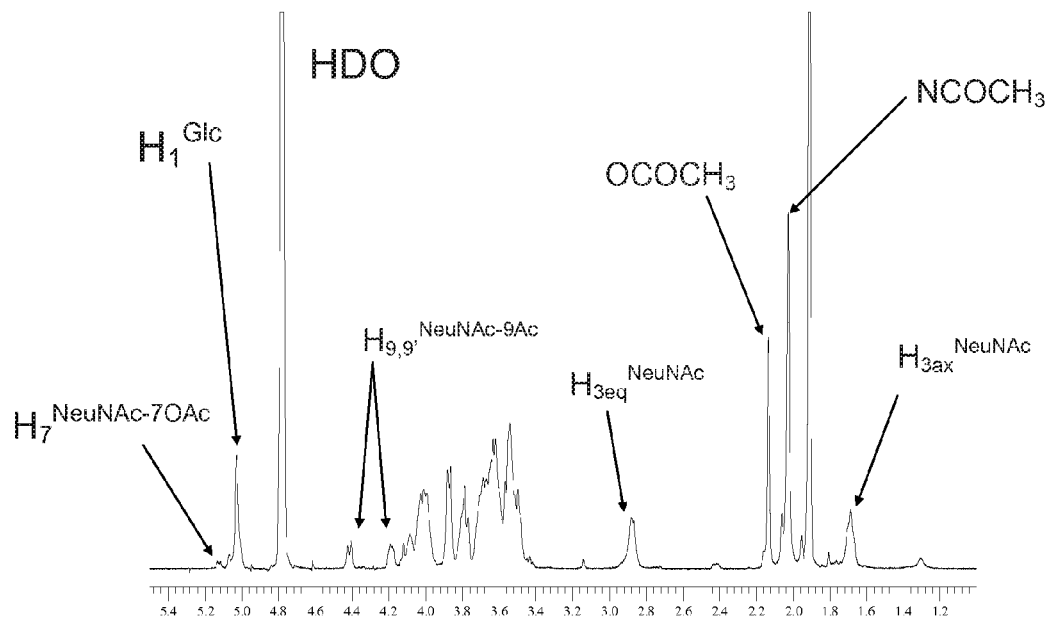

To show the peak assignment, annotated NMR spectra of hydrolysed MenW135 and hydrolysed MenY are presented in FIG. 1 and FIG. 2 respectively.

The following table gives the proportion of all sialic acid (N-acetyl-neuraminic acid) C7 and C9 positions in the population of saccharides derived from MenW135 that were found to be O-acetylated during conjugate preparation:

| Preparation step | % O-acetylation at 7 position | % O-acetylation at 9 position |
| --- | --- | --- |
| Native polysaccharide | 30.1 | 25.0 |
| After hydrolysis | 16.9 | 26.4 |
| Prior to amination | 15.0 | 26.2 |
| After activation | 5.1 | 26.3 |
| After conjugation | 6.3 | 43.1 |

Figure 3:
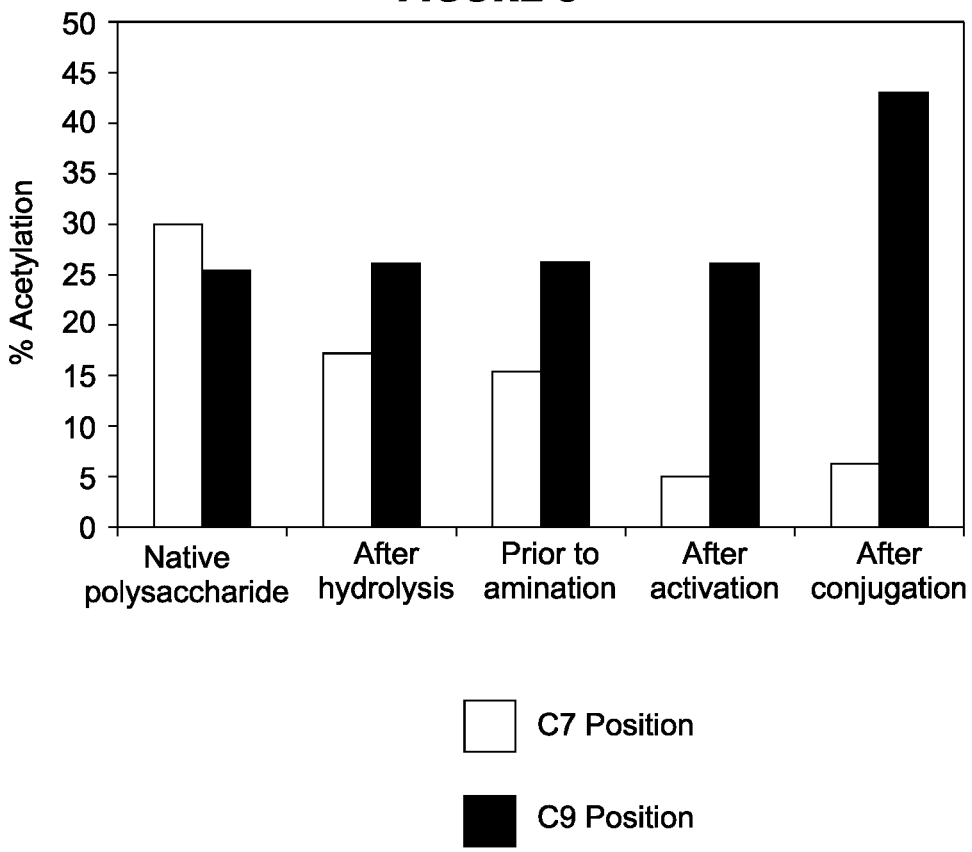
FIGS. 3 and 4 show the O-acetylation status of the sialic acid residues at the 7 and 9 positions during the preparation of MenW135-CRM$_{197}$ and MenY-CRM$_{197}$ conjugates, respectively.

Thus, the overall percentage of sialic acid O-acetylation at the 7 position fell during preparation of the conjugate, from about 30% to about 6%. At the same time, the percentage of O-acetylation at the 9 position increased from about 25% to about 43% (FIG. 3). The dramatic change seen at the 9 position in the final step shows that conjugation preferentially selects those saccharides that are O-acetylated at the 9 position.

Similarly, the O-acetylation status of the sialic acid residues in the population of modified saccharides derived from MenY after each step of the conjugation process is given in the following table:

| Preparation step | % O-acetylation at the 7 position | % O-acetylation at the 9 position |
| --- | --- | --- |
| Native polysaccharide | 10.3 | 28.0 |
| After hydrolysis | 3.3 | 24.1 |
| Prior to amination | 5.1 | 25.1 |
| After activation | 2.4 | 20.9 |
| After conjugation | 6.1 | 45.1 |

Figure 4:
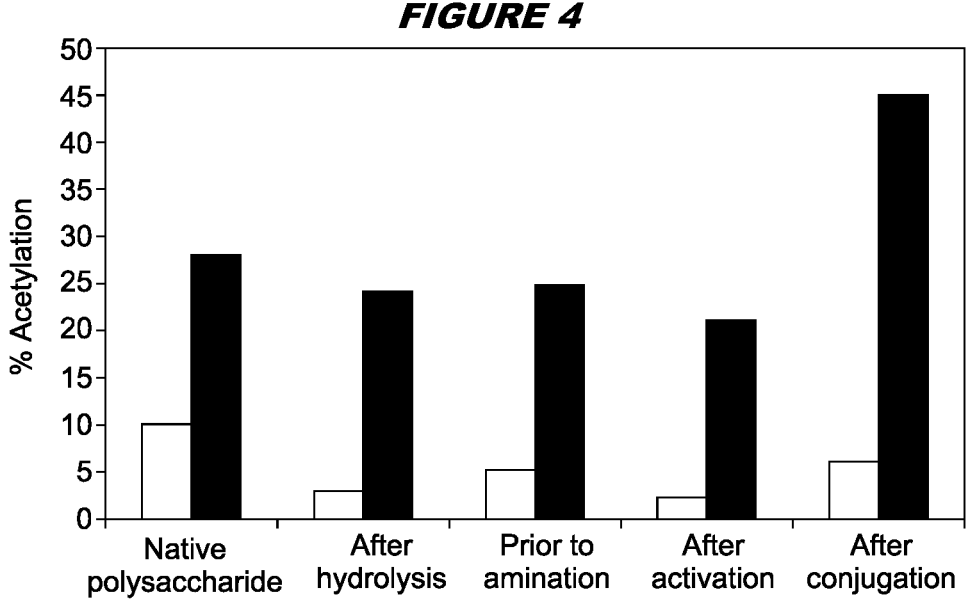

Thus, the percentage of sialic acid O-acetylation at the 7 position fell during preparation of the conjugate of the present invention from about 10% to about 2%, before finally rising to about 6% during the conjugation reaction. At the same time, the percentage of O-acetylation at the 9 position fell from about 28% to about 21%, before finally rising to about 45% during the conjugation reaction (FIG. 4). The dramatic change seen at the 9 position in the final step shows that conjugation preferentially selects those saccharides that are O-acetylated at the 9 position.

D. Immunogenicity of Conjugates

The frozen bulk conjugates were thawed. Each was diluted, under stirring, to a final concentration of 20 μg saccharide/ml, 5 mM phosphate, 9 mg/ml NaCl, aluminium phosphate (to give an $Al^{3+}$ concentration of 0.6 mg/ml), pH 7.2. The mixtures were then kept, without stirring, at 2-8° C. overnight and further diluted with saline to 4 μg saccharide/ml for mouse immunisation.

A second set of vaccines was prepared for both serogroups in the same way, but the addition of aluminium phosphate was replaced with same volume of water.

Ten Balb/c mice for each immunisation group were injected s.c. twice with 0.5 ml vaccine at weeks 0 and 4. Bleedings were performed before immunisation, the day before the second dose and 2 weeks after the second dose. Immunisations were performed with (a) the conjugate vaccine with or without alum, (b) saline control and (c) unconjugated polysaccharide control.

Specific anti-polysaccharide IgG antibodies were determined in the sera of immunised animals essentially as described in ref. 233. Each individual mouse serum was analysed in duplicate by a titration curve and GMT was calculated for each immunisation group. Titres were calculated in Mouse Elisa Units (MEU) using 'Titerun' software (FDA). Anti-polysaccharide titre specificity was determined by competitive ELISA with the relevant polysaccharide as competitor.

Figure 5:
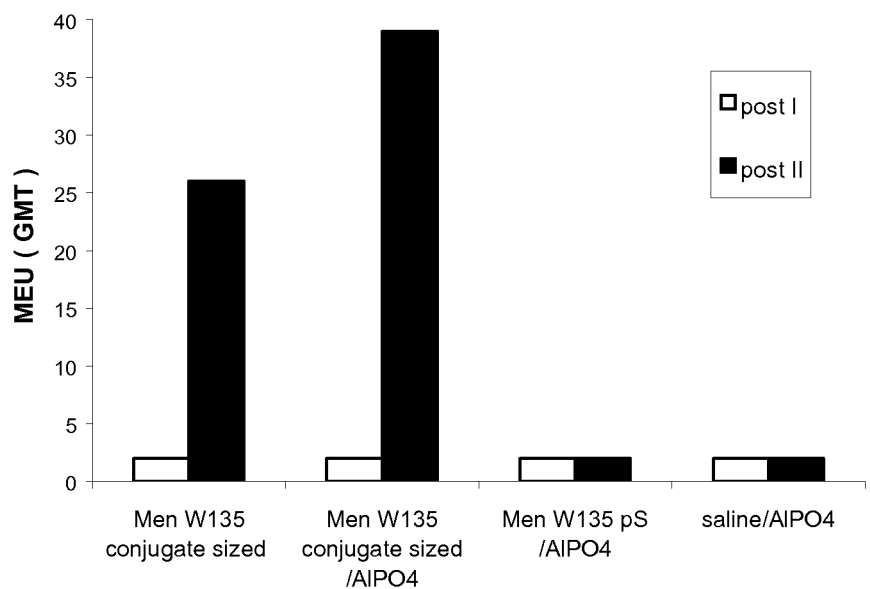
FIGS. 5 and 6 show IgG titres obtained in mice against oligosaccharide antigens using MenW135 and MenY, respectively.
Figure 6:
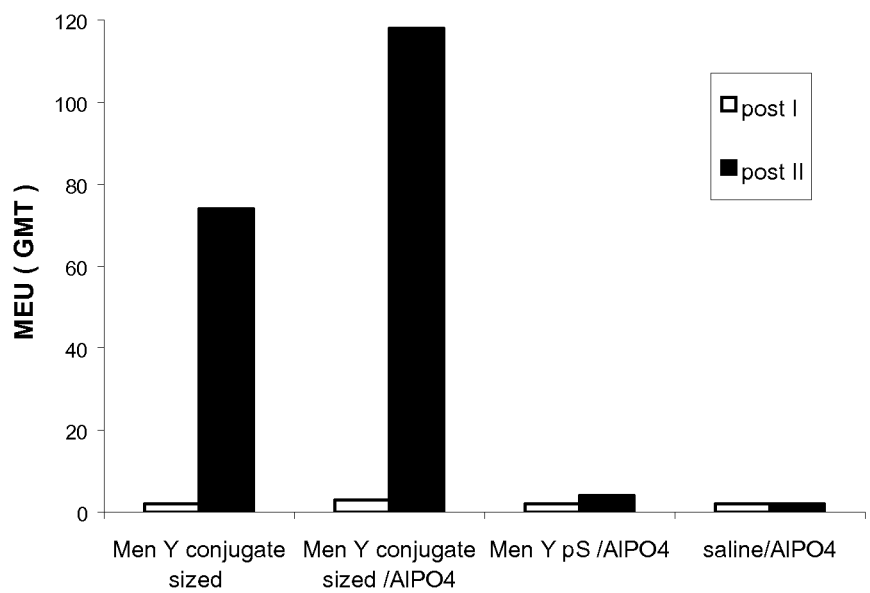

As shown in FIG. 5, the MenW135 conjugate induced high antibody titres in animals. As expected, the unconjugated polysaccharide was not immunogenic. The conjugate formulation with an aluminium phosphate as adjuvant induced a higher level of antibodies compared to the titre obtained by the conjugate alone. Similar results were seen for MenY (FIG. 6).

Post-II sera were tested for bactericidal activity using an in vitro assay to measure complement-mediated lysis of bacteria. Post-II sera were inactivated for 30 minutes at 56° C. before the use in the assay, and 25% baby rabbit complement was used as source of complement. Bactericidal titre was expressed as the reciprocal serum dilution yielding 50% killing of bacteria against the following strains: MenW135, 5554 (OAc+); MenY, 242975 (OAc+).

A capsular polysaccharide derived from MenW135 did not yield a GMT value and gave a bactericidal activity of only 4. In contrast, de-O-acetylated conjugates of the invention gave GMT values between 14 and 565, with bactericidal titres between 64 and 2048.

A capsular polysaccharide derived from MenY did not yield a GMT value and gave a bactericidal activity of only 256. In contrast, de-O-acetylated conjugates of the invention gave GMT values between 253 and 1618, with bactericidal titres between 256 and 16384.

It will be understood that the invention has been described by way of example only and modifications may be made whilst remaining within the scope and spirit of the invention. In particular, minor modifications that do not affect the immunogenicity of the modified capsular saccharide of the present invention are also encompassed.

REFERENCES

The Contents of which are Hereby Incorporated by Reference

[1] U.S. Pat. No. 4,711,779
[2] U.S. Pat. No. 4,761,283
[3] U.S. Pat. No. 4,882,317
[4] Lernercinier et al. (1996) *Carbohydr Res* 296: 83-96.
[5] Jones & Lernercinier (2002) *J Pharm Biomed Anal* 30:1233-47.
[6] Claus et al. (2004) *Molecular Microbiology* 51:227-39.
[7] Longworth et al. (2002) 13*th International Pathogenic Neisseria Conference*. Abstract, p. 272.
[8] Longworth et al. (2002) *FEMS Immunol Med Microbiol* 32:119-23.
[9] Pollard et al. (2003) *Emerging Infectious Diseases* 9:1503-4.
[10] Glode M. P. et al. (1979) *J Infect Dis* 139:52-56
[11] WO94/05325; U.S. Pat. No. 5,425,946.
[12] Berry et al. (2002) *Infect Immun* 70:3707-13.
[13] Frash (1990) p. 123-145 of *Advances in Biotechnological Processes* vol. 13 (eds. Mizrahi & Van Wezel)
[14] WO03/007985.
[15] Inzana (1987) *Infect. Immun.* 55:1573-1579.
[16] Ravenscroft et al. (1999) *Vaccine* 17:2802-2816.
[17] Kandil et al. (1997) *Glycoconj J* 14:13-17.
[18] Berkin et al. (2002) *Chemistry* 8:4424-4433.
[19] Ramsay et al. (2001) *Lancet* 357(9251): 195-6
[20] Lindberg (1999) *Vaccine* 17 Suppl 2:S28-36
[21] Buttery & Moxon (2000) *JR Coll Physicians Lond* 34:163-8
[22] Ahmad & Chapnick (1999) *Infect Dis Clin North Am* 13:113-33, vii
[23] Goldblatt (1998) *J. Med. Microbiol.* 47:563-567
[24] EP-B-0 477 508
[25] U.S. Pat. No. 5,306,492
[26] WO98/42721
[27] Dick et al. in *Conjugate Vaccines* (eds. Cruse et al.) Karger, Basel, 1989, Vol. 10, 48-114
[28] Hermanson *Bioconjugate Techniques*, Academic Press, San Diego Calif. (1996)
[29] Anonymous (January 2002) *Research Disclosure*, 453077.
[30] Anderson (1983) *Infect Immun* 39(1):233-238.
[31] Anderson et al. (1985) *J Clin Invest* 76(1):52-59.
[32] EP-A-0372501.
[33] EP-A-0378881.
[34] EP-A-0427347.
[35] WO93/17712
[36] WO94/03208.
[37] WO98/58668.
[38] EP-A-0471177.
[39] WO91/01146
[40] Falugi et al. (2001) *Eur J Immunol* 31:3816-3824.
[41] Baraldo et al, (2004) *Infect Immun.* 72:4884-7
[42] EP-A-0594610.
[43] WO00/56360.
[44] WO02/091998.
[45] Kuo et al. (1995) *Infect Immun* 63:2706-13.
[46] WO01/72337
[47] WO00/61761.
[48] WO2004/083251.
[49] WO99/42130
[50] WO96/40242
[51] Lees et al. (1996) *Vaccine* 14:190-198.
[52] WO95/08348.
[53] U.S. Pat. No. 4,695,624
[54] *Mol. Immunol.*, 1985, 22, 907-919
[55] EP-A-0208375
[56] Bethell G. S. et al., *J. Biol. Chem.*, 1979, 254, 2572-4
[57] Hearn M. T. W., *J. Chromatogr.*, 1981, 218, 509-18
[58] EP-A-0208375
[59] EP0720485
[60] EP0814833.
[61] WO00/10599
[62] Gever et al. (1979) *Med. Microbiol. Immunol* 165:171-288.
[63] U.S. Pat. No. 4,057,685.
[64] U.S. Pat. Nos. 4,673,574 & 4,808,700.
[65] U.S. Pat. No. 4,459,286.
[66] U.S. Pat. No. 4,965,338
[67] U.S. Pat. No. 4,663,160.
[68] U.S. Pat. No. 4,356,170
[69] Lei et al. (2000) *Dev Biol* (Basel) 103:259-264.
[70] WO00/38711; U.S. Pat. No. 6,146,902.
[71] WO00/56365
[72] Gennaro (2000) *Remington: The Science and Practice of Pharmacy*. 20th edition, ISBN: 0683306472.
[73] WO98/20734
[74] WO03/009869.
[75] *Vaccine design: the subunit and adjuvant approach* (1995) Powell & Newman. ISBN 0-306-44867-X.
[76] WO00/23105.
[77] WO90/14837.
[78] U.S. Pat. No. 5,057,540.
[79] WO 96/33739.
[80] EP-A-0109942.
[81] WO96/11711.
[82] WO00/07621.
[83] Barr et al. (1998) *Advanced Drug Delivery Reviews* 32:247-271.
[84] Sjolanderet et al. (1998) *Advanced Drug Delivery Reviews* 32:321-338.
[85] Niikura et al. (2002) *Virology* 293:273-280.
[86] Lenz et al. (2001) *J Immunol* 166:5346-5355.
[87] Pinto et al. (2003) *J Infect Dis* 188:327-338.
[88] Gerber et al. (2001) *Virol* 75:4752-4760.
[89] WO03/024480
[90] WO03/024481
[91] Gluck et al. (2002) *Vaccine* 20:B10-B16.
[92] EP-A-0689454.

[93] Johnson et al. (1999) *Bioorg Med Chem Lett* 9:2273-2278.
[94] Evans et al. (2003) *Expert Rev Vaccines* 2:219-229.
[95] Meraldi et al. (2003) *Vaccine* 21:2485-2491.
[96] Pajak et al. (2003) *Vaccine* 21:836-842.
[97] Kandimalla et al. (2003) *Nucleic Acids Research* 31:2393-2400.
[98] WO02/26757.
[99] WO99/62923.
[100] Krieg (2003) *Nature Medicine* 9:831-835.
[101] McCluskie et al. (2002) *FEMS Immunology and Medical Microbiology* 32:179-185.
[102] WO98/40100.
[103] U.S. Pat. No. 6,207,646.
[104] U.S. Pat. No. 6,239,116.
[105] U.S. Pat. No. 6,429,199.
[106] Kandimalla et al. (2003) *Biochemical Society Transactions* 31 (part 3):654-658.
[107] Blackwell et al. (2003) *J Immunol* 170:4061-4068.
[108] Krieg (2002) *Trends Immunol* 23:64-65.
[109] WO 01/95935.
[110] Kandimalla et al. (2003) *BBRC* 306:948-953.
[111] Bhagat et al. (2003) *BBRC* 300:853-861.
[112] WO03/035836.
[113] WO95/17211.
[114] WO98/42375.
[115] Beignon et al. (2002) *Infect Immun* 70:3012-3019.
[116] Pizza et al. (2001) *Vaccine* 19:2534-2541.
[117] Pizza et al. (2000) *Int J Med Microbiol* 290:455-461.
[118] Scharton-Kersten et al. (2000) *Infect Immun* 68:5306-5313.
[119] Ryan et al. (1999) *Infect Immun* 67:6270-6280.
[120] Partidos et al. (1999) *Immunol Lett* 67:209-216.
[121] Peppoloni et al. (2003) *Expert Rev Vaccines* 2:285-293.
[122] Pine et al. (2002) *J Control Release* 85:263-270.
[123] Domenighini et al. (1995) *Mol Microbiol* 15:1165-1167.
[124] WO99/44636.
[125] Singh et al] (2001) *J Cont Release* 70:267-276.
[126] WO99/27960.
[127] U.S. Pat. No. 6,090,406
[128] U.S. Pat. No. 5,916,588
[129] EP-A-0626169.
[130] WO99/52549.
[131] WO01/21207.
[132] WO01/21152.
[133] Andrianov et al. (1998) *Biomaterials* 19:109-115.
[134] Payne et al. (1998) *Adv Drug Delivery Review* 31:185-196.
[135] Stanley (2002) *Clin Exp Dermatol* 27:571-577.
[136] Jones (2003) *Curr Opin Investig Drugs* 4:214-218.
[137] WO99/11241.
[138] WO94/00153.
[139] WO98/57659.
[140] European patent applications 0835318, 0735898 and 0761231.
[141] WO99/24578.
[142] WO99/36544.
[143] WO99/57280.
[144] WO00/22430.
[145] WO01/64920.
[146] WO01/64922.
[147] WO03/020756.
[148] Tettelin et al. (2000) *Science* 287:1809-1815.
[149] WO96/29412.
[150] Pizza et al. (2000) *Science* 287:1816-1820.
[151] WO02/09643.
[152] Katial et al. (2002) *Infect Immun* 70:702-707.
[153] WO01/52885.
[154] European patent 0301992.
[155] Bjune et al. (1991) *Lancet* 338(8775):1093-1096.
[156] Fukasawa et al. (1999) *Vaccine* 17:2951-2958.
[157] WO02/09746.
[158] Rosenqvist et al. (1998) *Dev. Biol. Stand.* 92:323-333.
[159] WO01/09350.
[160] European patent 0449958.
[161] EP-A-0996712.
[162] EP-A-0680512.
[163] WO02/062378.
[164] WO99/59625.
[165] U.S. Pat. No. 6,180,111.
[166] WO01/34642.
[167] WO03/051379.
[168] U.S. Pat. No. 6,558,677
[169] WO2004/019977
[170] WO02/062380.
[171] WO00/25811.
[172] Peeters et al. (1996) *Vaccine* 14:1008-1015.
[173] Vermont et al. (2003) *Infect Immun* 71:1650-1655.
[174] Costantino et al. (1999) *Vaccine* 17:1251-1263.
[175] Bell (2000) *Pediatr Infect Dis J* 19:1187-1188.
[176] Iwarson (1995) *APMIS* 103:321-326.
[177] Gerlich et al. (1990) *Vaccine* 8 Suppl:S63-68 & 79-80.
[178] Gustafsson et al. (1996) *N. Engl. J. Med.* 334:349-355.
[179] Rappuoli et al. (1991) *TIBTECH* 9:232-238.
[180] *Vaccines* (1988) eds. Plotkin & Mortimer. ISBN 0-7216-1946-0.
[181] Del Guidice et al. (1998) *Molecular Aspects of Medicine* 19:1-70.
[182] Sutter et al. (2000) *Pediatr Clin North Am* 47:287-308.
[183] Zimmerman & Spann (1999) *Am Fam Physician* 59:113-118, 125-126.
[184] Robinson & Torres (1997) *Seminars in Immunology* 9:271-283.
[185] Donnelly et al. (1997) *Annu Rev Immunol* 15:617-648.
[186] Scott-Taylor & Dalgleish (2000) *Expert Opin Investig Drugs* 9:471-480.
[187] Apostolopoulos & Plebanski (2000) *Curr Opin Mol Ther* 2:441-447.
[188] Ilan (1999) *Curr Opin Mol Ther* 1:116-120.
[189] Dubensky et al. (2000) *Mol Med* 6:723-732.
[190] Robinson & Pertmer (2000) *Adv Virus Res* 55:1-74.
[191] Donnelly et al. (2000) *Am J Respir Crit Care Med* 162(4 Pt 2):S190-193.
[192] Davis (1999) *Mt. Sinai J. Med.* 66:84-90.
[193] Charalambous & Feavers (2001) *J Med Microbiol* 50:937-939.
[194] Westerink (2001) *Int Rev Immunol* 20:251-261.
[195] Grothaus et al. (2000) *Vaccine* 18:1253-1263.
[196] WO03/080678.
[197] WO98/08543.
[198] WO2004/032958, and UK patent applications 0223741.0, 0305831.0 & 0309115.4.
[199] http://neisseria.org/nm/typing/mlst/
[200] Pettersson et al. (1994) *Microb Pathog* 17(6):395-408.
[201] Maiden et al. (1998) *PNAS USA* 95:3140-3145.
[202] Welsch et al. (2002) 13th International Pathogenic Neisseria Conference, Norwegian Institute of Public Health, Oslo, Norway; Sep. 1-6, 2002. *Genome-derived antigen (GNA) 2132 elicits protective serum antibodies to groups B and C Neisseria meningitidis strains.*
[203] Santos et al. (2002) 13th International Pathogenic Neisseria Conference, Norwegian Institute of Public Health, Oslo, Norway; Sep. 1-6, 2002. *Serum bactericidal responses in rhesus macaques immunized with novel vaccines containing recombinant proteins derived from the genome of N. meningitidis.*
[204] Kanra et al. (1999) *The Turkish Journal of Paediatrics* 42:421-427.
[205] WO97/00697.
[206] WO02/00249.
[207] WO96/37222; U.S. Pat. No. 6,333,036.
[208] Watson (2000) *Pediatr Infect Dis J* 19:331-332.
[209] Rubin (2000) *Pediatr Clin North Am* 47:269-285, v.
[210] Jedrzejas (2001) *Microbiol Mol Biol Rev* 65:187-207.
[211] Zielen et al. (2000) *Infect. Immun.* 68:1435-1440.
[212] Darkes & Plosker (2002) *Paediatr Drugs* 4:609-630.
[213] Tettelin et al. (2001) *Science* 293:498-506.
[214] Hoskins et al (2001) *J Bacteriol* 183:5709-5717.
[215] Rappuoli (2000) *Curr Opin Microbiol* 3:445-450
[216] Rappuoli (2001) *Vaccine* 19:2688-2691.
[217] Masignani et al. (2002) *Expert Opin Biol Ther* 2:895-905.
[218] Mora et al. (2003) *Drug Discov Today* 8:459-464.
[219] Wizemann et al. (2001) *Infect Immun* 69:1593-1598.
[220] Rigden et al. (2003) *Crit Rev Biochem Mol Biol* 38:143-168.
[221] WO02/22167.
[222] WO01/30390.
[223] Almeida & Alpar (1996) *J. Drug Targeting* 3:455-467.
[224] Agarwal & Mishra (1999) *Indian J Exp Biol* 37:6-16.
[225] WO00/53221.
[226] Jakobsen et al. (2002) *Infect Immun* 70:1443-1452.
[227] Wu et al. (1997) *J Infect Dis* 175:839-846.
[228] Bergquist et al. (1998) *APMIS* 106:800-806.
[229] Baudner et al. (2002) *Infect Immun* 70:4785-4790.
[230] Ugozzoli et al. (2002) *J Infect Dis* 186:1358-1361.
[231] Miron & Wilchek (1982) *Anal. Biochem.* 126:433-435.
[232] Ravenscroft et al. (1999) *Vaccine* 17:2802-2816.
[233] Carlone et al (1992) *J. Clin. Microbiol.* 30:154-159.
[234] Kao & Tsai (2004) *Vaccine* 22:335-44.
[235] Cescutti et al. (1996) *Biochem Biophys Res Commun* 224:444-50.

---

What is claimed:

1. A modified serogroup Y meningococcal capsular saccharide, conjugated to a carrier protein, wherein (a) between 2-9% of the sialic acid residues in the saccharide are O-acetylated at the 7 position; and/or (b) between 35-55% of the sialic acid residues in the saccharide are O-acetylated at the 9 position.

2. The modified meningococcal capsular saccharide of claim 1 wherein between 4-8% of the sialic acid residues in the saccharide are O-acetylated at the 7 position.

3. The modified meningococcal capsular saccharide of claim 1, wherein between 40-50% of the sialic acid residues in the saccharide are O-acetylated at the 9 position.

4. A modified meningococcal capsular saccharide conjugated to a carrier protein, wherein the saccharide comprises n or more repeating units of the disaccharide unit:

[sialic acid]-[hexose]

wherein the hexose is glucose and n is an integer from 1 to 100, and wherein:

(a) x % of the sialic acid residues in said n or more repeating units are O-acetylated at the 7 position; and/or (b) y % of the sialic acid residues in said n or more repeating units are O-acetylated at the 9 position, wherein x is between 2-9 and y is between 35-55.

5. The saccharide of claim 4, wherein 6%±0.6% of the sialic acid residues in said n or more repeating units are O-acetylated at the 7 position, and 45%±4.5% of the sialic acid residues in said n or more repeating units are O-acetylated at the 9 position.

6. A composition comprising a molecules of serogroup Y meningococcal capsular saccharide, wherein (i) the average number of sialic acid residues per capsular saccharide molecule is b, and wherein: (a) between 2-9% of the a·b serogroup Y sialic acid residues in the composition are O-acetylated at the 7 position; and/or (b) between 35-55% of the a·b serogroup Y sialic acid residues in the composition are O-acetylated at the 9 position, (ii) the saccharide is conjugated to a carrier protein.

7. A saccharide comprising n or more repeats of the following disaccharide unit:

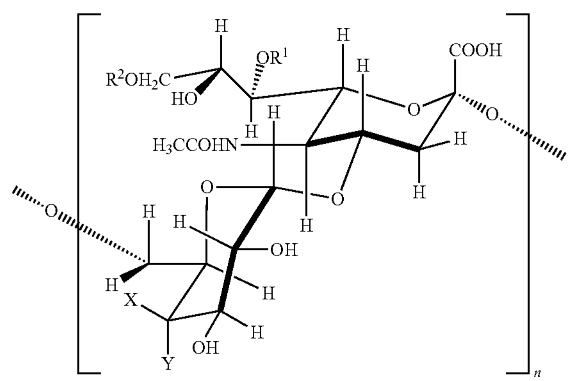

n is an integer from 1 to 100,

X and Y are different groups selected from —H and —OH, $R_1$ is independently selected from —H and —$COCH_3$ and may be the same or different in each disaccharide unit, $R_2$ is independently selected from —H and —$COCH_3$ and may be the same or different in each disaccharide unit, and, X is —H and Y is —OH, (a) 2-9% of $R_1$ are —$COCH_3$ and/or (b) 35-55% of $R_2$ are —$COCH_3$, and wherein the saccharide is conjugated to a carrier protein.

8. The saccharide of claim 1, wherein the saccharide has an average degree of polymerisation of less than 30.

9. The saccharide of claim 1, wherein the carrier protein is selected from the group consisting of: diphtheria toxoid, tetanus toxoid, *H. influenzae* protein D, and $CRM_{197}$.

10. An immunogenic composition comprising (a) a modified capsular saccharide conjugate of claim 1, and (b) a pharmaceutically acceptable carrier.

11. The composition of claim 10, in aqueous form.

12. The composition of claim 10, in lyophilised form.

13. The composition of claim 10, further comprising a capsular saccharide antigen from serogroup C of *N. meningitidis*.

14. The composition of claim 10, further comprising a capsular saccharide antigen from serogroup A of *N. meningitidis*.

15. The composition of claim 10, further comprising a capsular saccharide antigen from serogroup W135 of *N. meningitidis*.

16. The composition of claim 14, wherein the serogroup A antigen is a modified saccharide in which one or more of the hydroxyl groups on the native saccharide has/have been replaced by a blocking group.

17. The composition of claim 10, further comprising an antigen from serogroup B of *N. meningitidis*.

18. The composition of claim 10, further comprising a saccharide antigen from *Haemophilus influenzae* type B.

19. The composition of claim 10, further comprising an antigen from *Streptococcus pneumoniae*.

20. The composition of claim 10, further comprising one or more of: an antigen from hepatitis A virus; an antigen from hepatitis B virus; an antigen from *Bordetella pertussis*; a diphtheria toxoid; a tetanus toxoid; or a poliovirus antigen.

21. A method for raising an antibody response in a mammal, comprising administering a composition of claim 10 to the mammal.

22. A process for preparing a modified serogroup Y meningococcal capsular saccharide conjugated to a carrier protein comprising the steps of: (1) providing a starting serogroup Y meningococcal capsular saccharide and the carrier protein, either or both of which is/are optionally modified to render it/them reactive towards the other; (2) forming a covalent bond between the saccharide and the carrier protein; and (3) purifying the resulting serogroup Y meningococcal capsular saccharide conjugated to a carrier protein, wherein, between steps (1) and (3), the degree of O-acetylation at the 9 position of sialic acid residues in the starting saccharide increases to 35-55% and/or the degree of O-acetylation at the 7-position of the sialic acid residues decreases to 2-9% to generate the modified serogroup Y meningococcal capsular saccharide.

* * * * *

SEQUENCE LISTING

```
<160> NUMBER OF SEQ ID NOS: 5

<210> SEQ ID NO 1
<211> LENGTH: 327
<212> TYPE: PRT
<213> ORGANISM: Neisseria meningitidis

<400> SEQUENCE: 1

Ala Thr Asn Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
            20                  25                  30

Thr Ile Tyr Asp Ile Asp Glu Asp Gly Thr Ile Thr Lys Lys Asp Ala
        35                  40                  45

Thr Ala Ala Asp Val Glu Ala Asp Asp Phe Lys Gly Leu Gly Leu Lys
    50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
                100                 105                 110

Leu Asp Ala Thr Thr Asn Ala Leu Asn Lys Leu Gly Glu Asn Ile Thr
            115                 120                 125

Thr Phe Ala Glu Glu Thr Lys Thr Asn Ile Val Lys Ile Asp Glu Lys
        130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205

Glu Ala Ala Ala Gly Thr Ala Asn Thr Ala Ala Asp Lys Ala Glu Ala
    210                 215                 220
```

```
Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
            245                 250                 255

Glu Ser Asp Ser Lys Phe Val Arg Ile Asp Gly Leu Asn Ala Thr Thr
        260                 265                 270

Glu Lys Leu Asp Thr Arg Leu Ala Ser Ala Glu Lys Ser Ile Ala Asp
    275                 280                 285

His Asp Thr Arg Leu Asn Gly Leu Asp Lys Thr Val Ser Asp Leu Arg
290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325

<210> SEQ ID NO 2
<211> LENGTH: 644
<212> TYPE: PRT
<213> ORGANISM: Neisseria meningitidis

<400> SEQUENCE: 2

Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270
```

```
Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
                340                 345                 350

Gly Glu Met Leu Ala Gly Thr Ala Val Tyr Asn Gly Glu Val Leu His
                355                 360                 365

Phe His Thr Glu Asn Gly Arg Pro Ser Pro Ser Arg Gly Arg Phe Ala
370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
                420                 425                 430

Ser Gly Lys Phe Tyr Gly Pro Ala Gly Glu Glu Val Ala Gly Lys Tyr
                435                 440                 445

Ser Tyr Arg Pro Thr Asp Ala Glu Lys Gly Gly Phe Gly Val Phe Ala
        450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
                500                 505                 510

Phe Asp Gln Ala Lys Arg Asp Gly Lys Ile Asp Ile Thr Ile Pro Val
        515                 520                 525

Ala Asn Leu Gln Ser Gly Ser Gln His Phe Thr Asp His Leu Lys Ser
        530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
                580                 585                 590

Phe Asn Cys Tyr Gln Ser Pro Met Ala Lys Thr Glu Val Cys Gly Gly
                595                 600                 605

Asp Phe Ser Thr Thr Ile Asp Arg Thr Lys Trp Gly Val Asp Tyr Leu
                610                 615                 620

Val Asn Val Gly Met Thr Lys Ser Val Arg Ile Asp Ile Gln Ile Glu
625                 630                 635                 640

Ala Ala Lys Gln

<210> SEQ ID NO 3
<211> LENGTH: 434
<212> TYPE: PRT
<213> ORGANISM: Neisseria meningitidis

<400> SEQUENCE: 3
```

```
Met Val Ser Ala Val Ile Gly Ser Ala Ala Val Gly Ala Lys Ser Ala
1               5                   10                  15

Val Asp Arg Arg Thr Thr Gly Ala Gln Thr Asp Asn Val Met Ala
            20                  25                  30

Leu Arg Ile Glu Thr Thr Ala Arg Ser Tyr Leu Arg Gln Asn Asn Gln
            35                  40                  45

Thr Lys Gly Tyr Thr Pro Gln Ile Ser Val Val Gly Tyr Asn Arg His
            50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
                100                 105                 110

Thr Trp Asn Thr Ser Lys Val Arg Ala Thr Leu Leu Gly Ile Ser Pro
            115                 120                 125

Ala Thr Gln Ala Arg Val Lys Ile Val Thr Tyr Gly Asn Val Thr Tyr
            130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
                180                 185                 190

Ala Gly Leu Ala Asp Ala Leu Thr Ala Pro Leu Asp His Lys Asp Lys
            195                 200                 205

Gly Leu Gln Ser Leu Thr Leu Asp Gln Ser Val Arg Lys Asn Glu Lys
            210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
            275                 280                 285

Gln Thr Glu Gln Ile Gln Asp Ser Glu His Ser Gly Lys Met Val Ala
            290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
                340                 345                 350

Ala Lys Gln Gly Asn Gly Lys Ile Glu His Leu Lys Ser Pro Glu Leu
            355                 360                 365

Asn Val Asp Leu Ala Ala Asp Ile Lys Pro Asp Gly Lys Arg His
            370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415
```

-continued

Ala Glu Val Lys Thr Val Asn Gly Ile Arg His Ile Gly Leu Ala Ala
420 425 430

Lys Gln

<210> SEQ ID NO 4
<211> LENGTH: 6
<212> TYPE: DNA
<213> ORGANISM: Artificial Sequence
<220> FEATURE:
<223> OTHER INFORMATION: TLR9 motif

<400> SEQUENCE: 4 gtcgtt 6

<210> SEQ ID NO 5
<211> LENGTH: 6
<212> TYPE: DNA
<213> ORGANISM: Artificial Sequence
<220> FEATURE:
<223> OTHER INFORMATION: TLR9 motif

<400> SEQUENCE: 5 ttcgtt 6